United States Patent
Edgerton et al.

(10) Patent No.: US 11,298,533 B2
(45) Date of Patent: Apr. 12, 2022

(54) CONCERTED USE OF NONINVASIVE NEUROMODULATION DEVICE WITH EXOSKELETON TO ENABLE VOLUNTARY MOVEMENT AND GREATER MUSCLE ACTIVATION WHEN STEPPING IN A CHRONICALLY PARALYZED SUBJECT

(71) Applicant: The Regents of the University of California, Oakland, CA (US)

(72) Inventors: Victor Reggie Edgerton, Los Angeles, CA (US); Yury P. Gerasimenko, Los Angeles, CA (US); Parag Gad, Woodland Hills, CA (US)

(73) Assignee: The Regents of the University of California, Oakland, CA (US)

( * ) Notice: Subject to any disclaimer, the term of this patent is extended or adjusted under 35 U.S.C. 154(b) by 715 days.

(21) Appl. No.: 15/753,963

(22) PCT Filed: Aug. 26, 2016

(86) PCT No.: PCT/US2016/049129
§ 371 (c)(1),
(2) Date: Feb. 20, 2018

(87) PCT Pub. No.: WO2017/035512
PCT Pub. Date: Mar. 2, 2017

(65) Prior Publication Data
US 2018/0280693 A1    Oct. 4, 2018

Related U.S. Application Data

(60) Provisional application No. 62/210,070, filed on Aug. 26, 2015.

(51) Int. Cl.
*A61N 1/36* (2006.01)
*A61N 1/04* (2006.01)
(Continued)

(52) U.S. Cl.
CPC ............ *A61N 1/36003* (2013.01); *A61F 5/01* (2013.01); *A61G 5/14* (2013.01); *A61H 1/024* (2013.01);
(Continued)

(58) Field of Classification Search
CPC ............ A61N 1/36003; A61N 1/36034; A61N 1/0456; A61N 1/0476; A61N 1/0408;
(Continued)

(56) References Cited

U.S. PATENT DOCUMENTS 3,543,761 A    12/1970   Bradley
3,662,758 A    5/1972    Glover
(Continued)

FOREIGN PATENT DOCUMENTS

AU    2012204526 A1    7/2013
CA    2 823 592 A1     7/2012
(Continued)

OTHER PUBLICATIONS

U.S. Office Action dated Apr. 8, 2015 issued in U.S. Appl. No. 14/355,812.
(Continued)

*Primary Examiner* — Tammie K Marlen
(74) *Attorney, Agent, or Firm* — Tom Hunter; Weaver Austin Villeneuve & Sampson LLP

(57) ABSTRACT

In various embodiments a method of synergistically using a neuromodulation stimulator and a robotic exoskeleton for the restoration of voluntary movement and greater muscle activation in chronically paralyzed subjects is provided. The noninvasive neuromodulation system delivers signals to facilitate the restoration and/or enhancement of neurological function where at least one effect is strengthened stepping capacity that can be further substantiated when coupled with robotic exoskeleton assistance.

23 Claims, 6 Drawing Sheets

(51) Int. Cl.
    *A61F 5/01*     (2006.01)
    *A61H 1/02*     (2006.01)
    *A61H 3/00*     (2006.01)
    *A61G 5/14*     (2006.01)
    *B25J 9/00*     (2006.01)
    *A61H 3/02*     (2006.01)

(52) U.S. Cl.
CPC ......... *A61H 1/0244* (2013.01); *A61H 1/0262* (2013.01); *A61H 3/00* (2013.01); *A61N 1/0408* (2013.01); *A61N 1/0456* (2013.01); *A61N 1/0476* (2013.01); *A61N 1/0484* (2013.01); *A61N 1/36034* (2017.08); *B25J 9/0006* (2013.01); *A61H 1/0277* (2013.01); *A61H 1/0281* (2013.01); *A61H 3/02* (2013.01); *A61H 2201/10* (2013.01); *A61H 2201/1207* (2013.01); *A61H 2201/164* (2013.01); *A61H 2201/165* (2013.01); *A61H 2201/1614* (2013.01); *A61H 2201/1623* (2013.01); *A61H 2201/1628* (2013.01); *A61H 2201/1635* (2013.01); *A61H 2201/50* (2013.01); *A61H 2201/5025* (2013.01); *A61H 2201/5061* (2013.01); *A61H 2201/5064* (2013.01); *A61N 1/36031* (2017.08); *A61N 1/36057* (2013.01)

(58) Field of Classification Search
CPC .............. A61N 1/0484; A61N 1/36031; A61N 1/36057; A61H 1/0262; A61H 1/024; A61H 1/0244; A61H 1/0277; A61H 1/0281; A61H 2201/10; A61H 2201/1207; A61H 2201/1628; A61H 2201/1635; A61H 2201/164; A61H 2201/165; A61H 2201/5025; A61H 2201/5061; A61H 2201/5064; A61H 2201/1614; A61H 2201/1623; A61H 2201/50; A61H 3/00; A61H 3/02; B25J 9/0006; A61F 5/01; A61G 5/14
See application file for complete search history.

(56) References Cited

U.S. PATENT DOCUMENTS

| | | |
|---|---|---|
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,414,986 A | 11/1983 | Dickhudt et al. |
| 4,538,624 A | 9/1985 | Tarjan |
| 4,549,556 A | 10/1985 | Tajan et al. |
| 4,559,948 A | 12/1985 | Liss et al. |
| 4,573,481 A | 3/1986 | Bullara et al. |
| 4,800,898 A | 1/1989 | Hess et al. |
| 4,934,368 A | 6/1990 | Lynch |
| 4,969,452 A | 11/1990 | Petrofsky et al. |
| 5,002,053 A | 3/1991 | Garcia-Rill et al. |
| 5,031,618 A | 7/1991 | Mullett |
| 5,066,272 A | 11/1991 | Eaton et al. |
| 5,081,989 A | 1/1992 | Graupe et al. |
| 5,121,754 A | 6/1992 | Mullett |
| 5,344,439 A | 9/1994 | Otten |
| 5,354,320 A | 10/1994 | Schaldach et al. |
| 5,374,285 A | 12/1994 | Vaiani et al. |
| 5,417,719 A | 5/1995 | Hull et al. |
| 5,476,441 A | 12/1995 | Durfee et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,463,327 B1 | 10/2002 | Lurie et al. |
| 6,470,213 B1 | 10/2002 | Alley |
| 6,500,110 B1 | 12/2002 | Davey et al. |
| 6,503,231 B1 | 1/2003 | Prausnitz et al. |
| 6,505,074 B2 | 1/2003 | Boveja et al. |
| 6,516,227 B1 | 2/2003 | Meadows et al. |
| 6,551,849 B1 | 4/2003 | Kenney |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,819,956 B2 | 11/2004 | DiLorenzo |
| 6,839,594 B2 | 1/2005 | Cohen et al. |
| 6,862,479 B1 | 3/2005 | Whitehurst et al. |
| 6,871,099 B1 | 3/2005 | Whitehurst et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng et al. |
| 7,127,287 B2 | 10/2006 | Duncan et al. |
| 7,127,296 B2 | 10/2006 | Bradley |
| 7,127,297 B2 | 10/2006 | Law et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel et al. |
| 7,324,853 B2 | 1/2008 | Ayal et al. |
| 7,330,760 B2 | 2/2008 | Heruth et al. |
| 7,337,005 B2 | 2/2008 | Kim et al. |
| 7,337,006 B2 | 2/2008 | Kim et al. |
| 7,381,192 B2 | 6/2008 | Brodard et al. |
| 7,415,309 B2 | 8/2008 | Mcintyre |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| 7,544,185 B2 | 6/2009 | Bengtsson |
| 7,584,000 B2 | 9/2009 | Erickson |
| 7,590,454 B2 | 9/2009 | Garabedian et al. |
| 7,603,178 B2 | 10/2009 | North et al. |
| 7,628,750 B2 | 12/2009 | Cohen et al. |
| 7,660,636 B2 | 2/2010 | Castel et al. |
| 7,697,995 B2 | 4/2010 | Cross et al. |
| 7,729,781 B2 | 6/2010 | Swoyer et al. |
| 7,734,340 B2 | 6/2010 | De Ridder |
| 7,734,351 B2 | 6/2010 | Testerman et al. |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,813,809 B2 | 10/2010 | Strother et al. |
| 7,856,264 B2 | 12/2010 | Firlik et al. |
| 7,877,146 B2 | 1/2011 | Rezai et al. |
| 7,890,182 B2 | 2/2011 | Parramon et al. |
| 7,949,395 B2 | 5/2011 | Kuzma |
| 7,949,403 B2 | 5/2011 | Palermo et al. |

(56) References Cited

U.S. PATENT DOCUMENTS

| | | |
|---|---|---|
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,052 B2 | 1/2012 | Boling |
| 8,131,358 B2 | 3/2012 | Moffitt et al. |
| 8,155,750 B2 | 4/2012 | Jaax et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,214,048 B1 | 7/2012 | Whitehurst et al. |
| 8,229,565 B2 | 7/2012 | Kim et al. |
| 8,239,038 B2 | 8/2012 | Wolf, II |
| 8,260,436 B2 | 9/2012 | Gerber et al. |
| 8,271,099 B1 | 9/2012 | Swanson |
| 8,295,936 B2 | 10/2012 | Wahlstrand et al. |
| 8,311,644 B2 | 11/2012 | Moffitt et al. |
| 8,332,029 B2 | 12/2012 | Glukhovsky et al. |
| 8,346,366 B2 | 1/2013 | Arle et al. |
| 8,352,036 B2 | 1/2013 | DiMarco et al. |
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishmamurthy et al. |
| 8,588,884 B2 | 11/2013 | Hegde et al. |
| 8,700,145 B2 | 4/2014 | Kilgard et al. |
| 8,712,546 B2 | 4/2014 | Kim et al. |
| 8,750,957 B2 | 6/2014 | Tang et al. |
| 8,805,542 B2 | 8/2014 | Tai et al. |
| 9,072,891 B1 | 7/2015 | Rao |
| 9,101,769 B2 | 8/2015 | Edgerton et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,272,143 B2 | 3/2016 | Libbus et al. |
| 9,283,391 B2 | 3/2016 | Ahmed |
| 9,393,409 B2 | 7/2016 | Edgerton et al. |
| 9,409,023 B2 | 8/2016 | Burdick et al. |
| 9,415,218 B2 | 8/2016 | Edgerton et al. |
| 9,610,442 B2 | 4/2017 | Yoo et al. |
| 9,993,642 B2 | 6/2018 | Gerasimenko et al. |
| 10,137,299 B2 | 11/2018 | Lu et al. |
| 10,751,533 B2 | 8/2020 | Edgerton et al. |
| 10,773,074 B2 | 9/2020 | Liu et al. |
| 10,806,927 B2 | 10/2020 | Edgerton et al. |
| 11,097,122 B2 | 8/2021 | Lu |
| 11,123,312 B2 | 9/2021 | Lu et al. |
| 2002/0055779 A1 | 5/2002 | Andrews |
| 2002/0111661 A1 | 8/2002 | Cross et al. |
| 2002/0115945 A1 | 8/2002 | Herman et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0100933 A1 | 5/2003 | Ayal et al. |
| 2003/0158583 A1 | 8/2003 | Burnett et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0111118 A1 | 6/2004 | Hill et al. |
| 2004/0111126 A1 | 6/2004 | Tanagho et al. |
| 2004/0122483 A1 | 6/2004 | Nathan et al. |
| 2004/0127954 A1 | 7/2004 | McDonald, III |
| 2004/0133248 A1 | 7/2004 | Frei et al. |
| 2004/0138518 A1 | 7/2004 | Rise et al. |
| 2005/0004622 A1 | 1/2005 | Cullen et al. |
| 2005/0070982 A1 | 3/2005 | Heruth et al. |
| 2005/0075669 A1 | 4/2005 | King |
| 2005/0075678 A1 | 4/2005 | Faul |
| 2005/0102007 A1 | 5/2005 | Ayal et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0209655 A1 | 9/2005 | Bradley et al. |
| 2005/0246004 A1 | 11/2005 | Cameron et al. |
| 2005/0278000 A1 | 12/2005 | Strother et al. |
| 2006/0003090 A1 | 1/2006 | Rodger et al. |
| 2006/0041295 A1 | 2/2006 | Osypka |
| 2006/0089696 A1 | 4/2006 | Olsen et al. |
| 2006/0100671 A1 | 5/2006 | Ridder |
| 2006/0111754 A1 | 5/2006 | Rezai et al. |
| 2006/0122678 A1 | 6/2006 | Olsen et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0189839 A1 | 8/2006 | Laniado et al. |
| 2006/0239482 A1 | 10/2006 | Hatoum |
| 2006/0282127 A1 | 12/2006 | Zealear |
| 2007/0016097 A1 | 1/2007 | Farquhar et al. |
| 2007/0016266 A1 | 1/2007 | Paul, Jr. |
| 2007/0049814 A1 | 3/2007 | Muccio |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0073357 A1 | 3/2007 | Rooney et al. |
| 2007/0083240 A1 | 4/2007 | Peterson et al. |
| 2007/0156179 A1 | 7/2007 | S.E. |
| 2007/0168008 A1 | 7/2007 | Olsen |
| 2007/0179534 A1 | 8/2007 | Firlik et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0255372 A1 | 11/2007 | Metzler et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2008/0004674 A1 | 1/2008 | King et al. |
| 2008/0021513 A1 | 1/2008 | Thacker et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0103579 A1 | 5/2008 | Gerber |
| 2008/0140152 A1 | 6/2008 | Imran et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183224 A1 | 7/2008 | Barolat |
| 2008/0200749 A1 | 8/2008 | Zheng et al. |
| 2008/0202940 A1 | 8/2008 | Jiang et al. |
| 2008/0207985 A1 | 8/2008 | Farone |
| 2008/0215113 A1 | 9/2008 | Pawlowicz |
| 2008/0221653 A1 | 9/2008 | Agrawal et al. |
| 2008/0228241 A1 | 9/2008 | Sachs |
| 2008/0228250 A1 | 9/2008 | Mironer |
| 2008/0234791 A1 | 9/2008 | Arle et al. |
| 2008/0279896 A1 | 11/2008 | Heinen et al. |
| 2009/0012436 A1 | 1/2009 | Lanfermann et al. |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0157141 A1 | 6/2009 | Chiao et al. |
| 2009/0198305 A1 | 8/2009 | Naroditsky et al. |
| 2009/0204173 A1 | 8/2009 | Fang et al. |
| 2009/0270960 A1 | 10/2009 | Zhao et al. |
| 2009/0281599 A1 | 11/2009 | Thacker et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0023103 A1 | 1/2010 | Elborno |
| 2010/0042193 A1 | 2/2010 | Slavin |
| 2010/0070007 A1 | 3/2010 | Parker et al. |
| 2010/0114239 A1 | 5/2010 | McDonald et al. |
| 2010/0125313 A1 | 5/2010 | Lee et al. |
| 2010/0137938 A1 | 6/2010 | Kishawi et al. |
| 2010/0145428 A1 | 6/2010 | Cameron et al. |
| 2010/0152811 A1 | 6/2010 | Flaherty |
| 2010/0185253 A1 | 7/2010 | Dimarco et al. |

(56) References Cited

U.S. PATENT DOCUMENTS

| | | |
|---|---|---|
| 2010/0198298 A1 | 8/2010 | Glukhovsky et al. |
| 2010/0217355 A1 | 8/2010 | Tass et al. |
| 2010/0228310 A1 | 9/2010 | Shuros et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0305660 A1 | 12/2010 | Hegi et al. |
| 2010/0318168 A1 | 12/2010 | Bighetti |
| 2010/0331925 A1 | 12/2010 | Peterson |
| 2011/0029040 A1 | 2/2011 | Walker et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054579 A1 | 3/2011 | Kumar et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184488 A1 | 7/2011 | De Ridder |
| 2011/0184489 A1 | 7/2011 | Nicolelis et al. |
| 2011/0218594 A1 | 9/2011 | Doran et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224757 A1 | 9/2011 | Zdeblick et al. |
| 2011/0230701 A1 | 9/2011 | Simon et al. |
| 2011/0230702 A1 | 9/2011 | Honour |
| 2011/0245734 A1 | 10/2011 | Wagner et al. |
| 2011/0276107 A1 | 11/2011 | Simon et al. |
| 2011/0288609 A1 | 11/2011 | Tehrani et al. |
| 2011/0295100 A1 | 12/2011 | Rolston et al. |
| 2012/0006793 A1 | 1/2012 | Swanson |
| 2012/0029528 A1 | 2/2012 | Macdonald et al. |
| 2012/0035684 A1 | 2/2012 | Thompson et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0123293 A1 | 5/2012 | Shah et al. |
| 2012/0126392 A1 | 5/2012 | Kalvesten et al. |
| 2012/0165899 A1 | 6/2012 | Gliner |
| 2012/0172946 A1 | 7/2012 | Altaris et al. |
| 2012/0179222 A1 | 7/2012 | Jaax et al. |
| 2012/0185020 A1 | 7/2012 | Simon et al. |
| 2012/0197338 A1 | 8/2012 | Su et al. |
| 2012/0203055 A1 | 8/2012 | Pletnev |
| 2012/0221073 A1 | 8/2012 | Southwell et al. |
| 2012/0232615 A1 | 9/2012 | Barolat et al. |
| 2012/0252874 A1 | 10/2012 | Feinstein et al. |
| 2012/0259380 A1 | 10/2012 | Pyles |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0283797 A1 | 11/2012 | De Ridder |
| 2012/0302821 A1 | 11/2012 | Burnett |
| 2012/0310305 A1 | 12/2012 | Kaula et al. |
| 2012/0310315 A1 | 12/2012 | Savage et al. |
| 2012/0330391 A1 | 12/2012 | Bradley et al. |
| 2013/0012853 A1* | 1/2013 | Brown .................. A61F 5/026 602/19 |
| 2013/0013041 A1 | 1/2013 | Glukhovsky et al. |
| 2013/0030319 A1 | 1/2013 | Hettrick et al. |
| 2013/0030501 A1 | 1/2013 | Feler et al. |
| 2013/0053734 A1 | 2/2013 | Barriskill et al. |
| 2013/0053922 A1 | 2/2013 | Ahmed et al. |
| 2013/0066392 A1 | 3/2013 | Simon et al. |
| 2013/0085317 A1 | 4/2013 | Feinstein |
| 2013/0110196 A1 | 5/2013 | Alataris et al. |
| 2013/0123568 A1 | 5/2013 | Hamilton et al. |
| 2013/0123659 A1 | 5/2013 | Bartol et al. |
| 2013/0165991 A1 | 6/2013 | Kim et al. |
| 2013/0197408 A1 | 8/2013 | Goldfarb et al. |
| 2013/0204324 A1 | 8/2013 | Thacker et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268021 A1 | 10/2013 | Moffitt |
| 2013/0281890 A1 | 10/2013 | Mishelevich |
| 2013/0289446 A1 | 10/2013 | Stone et al. |
| 2013/0303873 A1 | 11/2013 | Voros et al. |
| 2013/0304159 A1 | 11/2013 | Simon et al. |
| 2013/0310911 A1 | 11/2013 | Tai et al. |
| 2014/0031893 A1 | 1/2014 | Walker et al. |
| 2014/0046407 A1 | 2/2014 | Ben-Ezra et al. |
| 2014/0058490 A1 | 2/2014 | DiMarco |
| 2014/0066950 A1 | 3/2014 | Macdonald et al. |
| 2014/0067007 A1 | 3/2014 | Drees et al. |
| 2014/0067354 A1 | 3/2014 | Kania et al. |
| 2014/0081071 A1 | 3/2014 | Simon et al. |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0163640 A1 | 6/2014 | Edgerton et al. |
| 2014/0180361 A1 | 6/2014 | Burdick et al. |
| 2014/0213842 A1 | 7/2014 | Simon et al. |
| 2014/0236257 A1 | 8/2014 | Parker et al. |
| 2014/0296752 A1 | 10/2014 | Edgerton et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0336722 A1* | 11/2014 | Rocon De Lima ......................... A61N 1/36067 607/45 |
| 2014/0357936 A1 | 12/2014 | Simon et al. |
| 2015/0005840 A1 | 1/2015 | Pal et al. |
| 2015/0065559 A1 | 3/2015 | Feinstein et al. |
| 2015/0165226 A1 | 6/2015 | Simon et al. |
| 2015/0182784 A1 | 7/2015 | Barriskill et al. |
| 2015/0190634 A1 | 7/2015 | Rezai et al. |
| 2015/0231396 A1 | 8/2015 | Burdick et al. |
| 2015/0265830 A1 | 9/2015 | Simon et al. |
| 2016/0030737 A1 | 2/2016 | Gerasimenko et al. |
| 2016/0030748 A1 | 2/2016 | Edgerton et al. |
| 2016/0045727 A1 | 2/2016 | Rezai et al. |
| 2016/0045731 A1 | 2/2016 | Simon et al. |
| 2016/0074663 A1 | 3/2016 | De Ridder |
| 2016/0121109 A1 | 5/2016 | Edgerton et al. |
| 2016/0121114 A1 | 5/2016 | Simon et al. |
| 2016/0121116 A1 | 5/2016 | Simon et al. |
| 2016/0175586 A1 | 6/2016 | Edgerton et al. |
| 2016/0220813 A1 | 8/2016 | Edgerton et al. |
| 2016/0235977 A1 | 8/2016 | Lu et al. |
| 2016/0271413 A1 | 9/2016 | Vallejo et al. |
| 2016/0339239 A1 | 11/2016 | Yoo et al. |
| 2017/0007831 A1 | 1/2017 | Edgerton et al. |
| 2017/0157389 A1 | 6/2017 | Tai et al. |
| 2017/0161454 A1 | 6/2017 | Grill et al. |
| 2017/0165497 A1 | 6/2017 | Lu |
| 2017/0246450 A1 | 8/2017 | Liu et al. |
| 2017/0246452 A1 | 8/2017 | Liu et al. |
| 2017/0274209 A1 | 9/2017 | Edgerton et al. |
| 2017/0296837 A1 | 10/2017 | Jin |
| 2018/0125416 A1 | 5/2018 | Schwarz et al. |
| 2018/0185642 A1 | 7/2018 | Lu |
| 2018/0256906 A1 | 9/2018 | Pivonka et al. |
| 2018/0361146 A1 | 12/2018 | Gerasimenko et al. |
| 2019/0022371 A1 | 1/2019 | Chang et al. |
| 2019/0167987 A1 | 6/2019 | Lu et al. |
| 2019/0381313 A1 | 12/2019 | Lu |
| 2020/0155865 A1 | 5/2020 | Lu |
| 2021/0187278 A1 | 6/2021 | Lu |
| 2021/0236837 A1 | 8/2021 | Lu |

FOREIGN PATENT DOCUMENTS

| | | |
|---|---|---|
| CA | 2 856 202 A1 | 5/2013 |
| CA | 2 864 473 A1 | 5/2013 |
| CN | 101227940 A | 7/2008 |
| CN | 103263727 A | 8/2013 |
| CN | 104307098 A | 1/2015 |

(56) References Cited

FOREIGN PATENT DOCUMENTS

| | | |
|---|---|---|
| EP | 2661307 A2 | 11/2013 |
| EP | 2968940 A1 | 1/2016 |
| JP | H03-26620 A | 2/1991 |
| JP | 2007-526798 A | 9/2007 |
| JP | 2008-543429 A | 12/2008 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2575283 C2 | 2/2013 |
| WO | WO 97/047357 A1 | 12/1997 |
| WO | WO 03/026735 A2 | 4/2003 |
| WO | WO 03/092795 A1 | 11/2003 |
| WO | WO 2004/087116 A2 | 10/2004 |
| WO | WO 2005/051306 A2 | 6/2005 |
| WO | WO 2005/065768 A1 | 7/2005 |
| WO | WO 2005/087307 A2 | 9/2005 |
| WO | WO 2006/138069 A1 | 12/2006 |
| WO | WO 2007/007058 A1 | 1/2007 |
| WO | WO 2007/012114 A1 | 2/2007 |
| WO | WO 2007/107831 A2 | 9/2007 |
| WO | WO 2008/109862 A1 | 9/2008 |
| WO | WO 2009/111142 A2 | 9/2009 |
| WO | WO 2010/055421 A1 | 5/2010 |
| WO | WO 2010/114998 A1 | 10/2010 |
| WO | WO 2010/124128 A1 | 10/2010 |
| WO | WO 2012/094346 A2 | 7/2012 |
| WO | WO 2012/100260 A2 | 7/2012 |
| WO | WO 2012/129574 A2 | 9/2012 |
| WO | WO 2013/071307 A1 | 5/2013 |
| WO | WO 2013/071309 A1 | 5/2013 |
| WO | WO 2013/188965 A1 | 12/2013 |
| WO | WO 2014/144785 A1 | 9/2014 |
| WO | WO 2015/048563 A2 | 4/2015 |
| WO | WO 2016/029159 A2 | 2/2016 |
| WO | WO 2016/033369 A1 | 3/2016 |
| WO | WO 2016/033372 A1 | 3/2016 |
| WO | WO 2017/011410 A1 | 1/2017 |
| WO | WO 2017/024276 A1 | 2/2017 |
| WO | WO 2017/035512 A1 | 3/2017 |
| WO | WO 2017/044904 A1 | 3/2017 |
| WO | WO 2018/106843 A1 | 6/2018 |
| WO | WO 2018/140531 A1 | 8/2018 |
| WO | WO 2018/217791 A1 | 11/2018 |
| WO | WO 2020/041502 A1 | 2/2020 |
| WO | WO 2020/041633 A1 | 2/2020 |
| WO | WO 2020/236946 A1 | 11/2020 |
| XK | WO 2008/121891 A1 | 10/2008 |
| XK | WO 2009/042217 A1 | 4/2009 |

OTHER PUBLICATIONS

U.S. Final Office Action dated Sep. 21, 2015 issued in U.S. Appl. No. 14/355,812.
U.S. Notice of Allowance dated Apr. 13, 2016 issued in U.S. Appl. No. 14/355,812.
U.S. Office Action dated Oct. 18, 2016 issued in U.S. Appl. No. 15/208,529.
U.S. Final Office Action dated Jul. 13, 2017 issued in U.S. Appl. No. 15/208,529.
U.S. Office Action dated Jul. 27, 2018 issued in U.S. Appl. No. 15/208,529.
U.S. Final Office Action dated Apr. 19, 2019 issued in U.S. Appl. No. 15/208,529.
U.S. Office Action dated Oct. 28, 2019 issued in U.S. Appl. No. 15/208,529.
U.S. Office Action dated Oct. 3, 2017 issued in U.S. Appl. No. 15/025,201.
U.S. Notice of Allowance dated Aug. 1, 2018 issued in U.S. Appl. No. 15/025,201.
U.S. Office Action dated Apr. 10, 2020 issued in U.S. Appl. No. 16/200,467.
U.S. Office Action dated Jul. 13, 2016 issued in U.S. Appl. No. 14/775,618.
U.S. Final Office Action dated Apr. 25, 2017 issued in U.S. Appl. No. 14/775,618.
U.S. Notice of Allowance dated Jan. 18, 2018 issued in U.S. Appl. No. 14/775,618.
U.S. Office Action dated Jan. 8, 2020 issued in U.S. Appl. No. 15/975,678.
U.S. Office Action dated Oct. 31, 2019 issued in U.S. Appl. No. 15/750,499.
U.S. Office Action dated Jul. 22, 2019 issued in U.S. Appl. No. 15/506,696.
U.S. Office Action dated Jun. 4, 2019 issued in U.S. Appl. No. 15/505,053.
U.S. Notice of Allowance dated Feb. 13, 2020 issued in U.S. Appl. No. 15/505,053.
U.S. Office Action dated Apr. 17, 2019 issued in U.S. Appl. No. 15/344,381.
U.S. Final Office Action dated Dec. 30, 2019 issued in U.S. Appl. No. 15/344,381.
PCT International Search Report dated Jul. 30, 2012 issued in PCT/US2012/020112.
PCT International Preliminary Report on Patentability and Written Opinion dated Jul. 10, 2013 issued in PCT/US2012/020112.
PCT International Search Report and Written Opinion dated Mar. 19, 2013 issued in PCT/US2012/064878.
PCT International Preliminary Report on Patentability dated May 22, 2014 issued in PCT/US2012/064878.
Australian Patent Examination Report No. 1 dated Jul. 11, 2016 issued in AU 2012334926.
Canadian Office Action dated Aug. 31, 2018 issued in CA 2,864,473.
Canadian Office Action dated Jul. 30, 2019 issued in CA 2,864,473.
European Communication pursuant to Rule 114(2) EPC regarding observations by a third party dated Mar. 27, 2015 issued in EP 12 847 885.6.
European Extended Search Report dated May 6, 2015 issued in EP 12 847 885.6.
European Office Action dated Apr. 15, 2016 issued in EP 12 847 885.6.
European Reply to Communication of Apr. 15, 2016 dated Oct. 24, 2016 in EP 12 847 885.6.
European Second Office Action dated Feb. 16, 2017 issued in EP 12 847 885.6.
PCT Declaration of Non-Establishment of International Search Report and Written Opinion dated Dec. 24, 2014 issued in PCT/US2014/057886.
PCT International Preliminary Report on Patentability and Written Opinion dated Apr. 7, 2016 issued in PCT/US2014/057886.
Australian Examination report No. 1 dated Jan. 11, 2019 issued in AU 2014324660.
Australian Examination report No. 2 dated Nov. 7, 2019 issued in AU 2014324660.
Australian Examination report No. 3 dated Jan. 6, 2020 issued in AU 2014324660.
European Extended Search Report dated May 10, 2017 issued in EP 14849355.4.
European Office Action dated Jul. 20, 2018 issued in EP 14849355.4.
PCT International Search Report and Written Opinion dated Aug. 6, 2014 issued in PCT/US2014/029340.
PCT International Preliminary Report on Patentability dated Sep. 24, 2015 issued in PCT/US2014/029340.

(56) References Cited

OTHER PUBLICATIONS

Australian Patent Examination Report No. 1 dated May 11, 2018 issued in AU 2014228794.
Australian Patent Examination Report No. 1 dated Jan. 6, 2020 issued in AU 2019206059.
European Extended Search Report dated Nov. 8, 2016 issued in EP 14765477.6.
European Office Action dated Nov. 14, 2018 issued in EP 14765477.6.
European Office Action dated Sep. 27, 2019 issued in EP 14765477.6.
PCT International Search Report and Written Opinion dated Dec. 5, 2016 issued in PCT/US2016/045898.
PCT International Preliminary Report on Patentability and Written Opinion dated Feb. 15, 2018 issued in PCT/US2016/045898.
European Extended Search Report dated Dec. 13, 2018 issued in EP 16833973.7.
PCT International Search Report and Written Opinion dated Dec. 8, 2015 issued in PCT/US2015/047268.
PCT International Preliminary Report on Patentability and Written Opinion dated Feb. 28, 2017 issued in PCT/US2015/047268.
Australian Patent Examination Report No. 1 dated Jul. 18, 2019 issued in AU 2015308779.
European Extended Search Report dated Mar. 1, 2018 issued in EP 15836927.2.
European Extended Search Report dated Apr. 21, 2020 issued in EP 19201998.2.
PCT International Search Report and Written Opinion dated Dec. 3, 2015 issued in PCT/US2015/047272.
PCT International Preliminary Report on Patentability and Written Opinion dated Feb. 28, 2017 issued in PCT/US2015/047272.
PCT Declaration of Non-Establishment of International Search Report and Written Opinion dated Dec. 1, 2015 issued in PCT/US2015/046378.
PCT International Preliminary Report on Patentability and Written Opinion dated Feb. 21, 2017 issued in PCT/US2015/046378.
Australian Patent Examination Report No. 1 dated Jun. 14, 2019 issued in AU 2015305237.
Australian Patent Examination Report No. 2 dated Apr. 17, 2020 issued in AU 2015305237.
European Extended Search Report dated Apr. 4, 2018 issued in EP 15834593.4.
European Office Action dated Jul. 17, 2019 issued in EP 15834593.4.
PCT International Search Report and Written Opinion dated Sep. 12, 2016 issued in PCT/US2016/041802.
PCT International Preliminary Report on Patentability and Written Opinion dated Jan. 25, 2018 issued in PCT/US2016/041802.
European Extended Search Report dated Feb. 19, 2019 issued in EP 16825005.8.
PCT International Search Report and Written Opinion dated Dec. 5, 2016 issued in PCT/US2016/049129.
PCT International Preliminary Report on Patentability and Written Opinion dated Mar. 8, 2018 issued in PCT/US2016/049129.
PCT International Search Report and Written Opinion dated Mar. 12, 2018 issued in PCT/US2018/015098.
PCT International Preliminary Report on Patentability and Written Opinion dated Jul. 30, 2019 issued in PCT/US2018/015098.
PCT International Search Report and Written Opinion dated Aug. 31, 2018 issued in PCT/US2018/033942.
PCT International Preliminary Report on Patentability and Written Opinion dated Nov. 26, 2019 issued in PCT/US2018/033942.
PCT International Search Report and Written Opinion dated Nov. 14, 2019 issued in PCT/US2019/047777.
PCT International Search Report and Written Opinion dated Nov. 21, 2019 issued in PCT/US2019/047551.
PCT International Search Report dated Mar. 19, 2013 issued in PCT/US2012/064874.
PCT International Search Report dated Mar. 19, 2013 issued in PCT/US2012/064878.
PCT International Search Report dated Sep. 3, 2012 issued in PCT/US2012/022257.
PCT International Search Report dated Oct. 31, 2012 issued in PCT/US2012/030624.
Andersson, et al., (2003) "CNS Involvement in Overactive Bladder." *Drugs*, 63(23): 2595-2611.
Angeli et al. (2014) "Altering spinal cord excitability enables voluntary movements after chronic complete paralysis in humans" *Brain* 137: 1394-1409.
Courtine, Grégoire et al. (2007) "Modulation of multisegmental monosynaptic responses in a variety of leg muscles during walking and running in humans," *J Physiol.* 582.3:1125-1139.
Danner S.M., Hofstoetter U.S., Ladenbauer J., Rattay F., and Minassian K. (Mar. 2011) "Can the human lumbar posterior column be stimulated by transcutaneous spinal cord stimulation? A modeling study" *Europe PMC Funders Author Manuscripts, Artif Organs* 35(3):257-262, 12 pp.
DeSantana et al. (Dec. 2008) "Effectiveness of Transcutaneous Electrical Nerve Stimulation for Treatment of Hyperalgesia and Pain," *Curr Rheumatol Rep.* 10(6):492-499, 12 pp.
Dubinsky, Richard M. and Miyasaki, Janis, "Assessment: Efficacy of transcutaneous electric nerve stimulation in the treatment of pain in neurologic disorders (an evidence-based review)," Report of the Therapeutics and Technology Assessment Subcommittee of the American Academy of Neurology, (2010) *Neurology,* 74:173-176.
Edgerton and Harkema (2011) "Epidural stimulation of the spinal cord in spinal cord injury: current status and future challenges" *Expert Rev Neurother.* 11(10): 1351-1353. doi:10.1586/ern.11.129 [NIH Public Access—Author Manuscript—5 pages].
Fong et al. (2009) "Recovery of control of posture and locomotion after a spinal cord injury: solutions staring US in the face," *Progress in Brain Research,* Elsevier Amsterdam, NL, 175:393-418.
Ganley et al., (2005) "Epidural Spinal Cord Stimulation Improves Locomoter Performance in Low ASIA C, Wheelchair-Dependent, Spinal Cord-Injured Individuals: Insights from Metabolic Response," *Top. Spinal Cord Inj. Rehabil;* 11 (2):50-63.
Gerasimenko Y., Gorodnichev R., Machueva E., Pivovarova E., Semyenov D., Savochin A., Roy R.R., and Edgerton V.R., (Mar. 10, 2010) "Novel and Direct Access to the Human Locomotor Spinal Circuitry," *J Neurosci.* 30(10):3700-3708, PMC2847395.
Gerasimenko Y.P., Ichiyama R.M., Lavrov I.A., Courtine G., Cai L., Zhong H., Roy R.R., and Edgerton V.R. (2007) "Epidural Spinal Cord Stimulation Plus Quipazine Administration Enable Stepping in Complete Spinal Adult Rats," *J Neurophysiol.* 98:2525-2536.
Harkema et al. (2011) "Effect of Epidural stimulation of the lumbosacral spinal cord on voluntary movement, standing, and assisted stepping after motor complete paraplegia: a case study" *Lancet* 377(9781): 1938-1947; NIH Public Access Author Manuscript 17 pages [doi:10.1016/S0140-6736(11)60547-3].
Herman R., He J., D'Luzansky S., Willis W., Dilli S., (2002) "Spinal cord stimulation facilitates functional walking in a chronic, incomplete spinal cord injured," *Spinal Cord.* 40:65-68.
Hofstoetter, U.S. et al. (Aug. 2008) "Modification of Reflex Responses to Lumbar Posterior Root Stimulation by Motor Tasks in Healthy Subjects," *Artif Organs,* 32(8):644-648.
Ichiyama et al. (2005) "Hindlimb stepping movements in complete spinal rats induced by epidural spinal cord stimulation" *Neuroscience Letters,* 383:339-344.
Kapetanakis, et al. (2017) "Cauda Equina Syndrome Due to Lumbar Disc Herniation: a Review of Literature," *Folia Medica,* 59(4): 377-86.
Kitano K., Koceja D.M. (2009) "Spinal reflex in human lower leg muscles evoked by transcutaneous spinal cord stimulation," *J Neurosci Methods.* 180:111-115.
Minasian et al. (2010) "Transcutaneous stimulation of the human lumbar spinal cord: Facilitating locomotor output in spinal cord injury," *Conf. Proceedings Soc. for Neurosci.,* Abstract No. 286.19, 1 page.
Minassian et al. (Aug. 2011) "Transcutaneous spinal cord stimulation," *International Society for Restorative Neurology,* http://restorativeneurology.org/resource-center/assessments/transcutaneous-

(56) References Cited

OTHER PUBLICATIONS lumbar-spinal-cord-stimulation/; http://restorativeneurology.org/wp-content/uploads/2011/08/Transcutaneous-spinal-cord-stimulation_long.pdf, 6 pp.

Minassian et al. (Mar. 2007) "Posterior root-muscle reflexes elicited by transcutaneous stimulation of the human lumbosacral cord," *Muscle & Nerve* 35:327-336.

Nandra et al., (2014) "Microelectrode Implants for Spinal Cord Stimulation in Rats," *Thesis, California Institute of Technology,* Pasadena, California, Defended on Sep. 24, 2014, 104 pages.

Nandra et al., (Jan. 23, 2011) "A Parylene-Based Microelectrode Arrary Implant for Spinal Cord Stimulation in Rats," *Conf. Proc. IEEE Eng. Med. Biol. Soc.*, pp. 1007-1010.

Rodger et al., (2007) "High Density Flexible Parylene-Based Multielectrode Arrays for Retinal and Spinal Cord Stimulation," Transducers & Eurosensors, Proc. Of the 14th International Conference on Solid-State Sensors, Actuators and Microsystems, Lyon, France, Jun. 10-14, 2007, *IEEE,* pp. 1385-1388.

Seifert et al. (Nov. 1, 2002) "Restoration of Movement Using Functional Electrical Stimulation and Bayes' Theorem," *The Journal of Neuroscience,* 22(1):9465-9474.

Tanabe et al. (2008) "Effects of transcutaneous electrical stimulation combined with locomotion-like movement in the treatment of post-stroke gait disorder: a single-case study," 30(5):411-416 abstract, 1 page.

Wang, et al. (2017) "Incidence of C5 nerve root palsy after cervical surgery," *Medicine,* 96(45), 14 pages.

Ward, Alex R. (Feb. 2009) "Electrical Stimulation Using Kilohertz-Frequency Alternating Current," (2009) *Phys Ther.*89(2):181-190 [published online Dec. 18, 2008].

U.S. Notice of Allowance dated Jun. 17, 2020 issued in U.S. Appl. No. 15/208,529.

U.S. Final Office Action dated Jul. 29, 2020 issued in U.S. Appl. No. 15/975,678.

U.S. Final Office Action dated Aug. 6, 2020 issued in U.S. Appl. No. 15/750,499.

U.S. Notice of Allowance dated May 4, 2020 issued in U.S. Appl. No. 15/506,696.

U.S. 2nd Notice of Allowance dated Jun. 4, 2020 issued in U.S. Appl. No. 15/505,053.

U.S. Office Action dated Apr. 7, 2020 issued in U.S. Appl. No. 15/740,323.

U.S. Office Action dated Aug. 4, 2020 issued in U.S. Appl. No. 15/344,381.

Canadian Office Action dated Aug. 14, 2020 issued in CA 2,864,473.

Canadian Office Action dated May 7, 2020 issued in CA 2,906,779.

Australian Patent Examination Report No. 2 dated May 20, 2020 issued in AU 2015308779.

European Office Action dated Jul. 30, 2020 issued in EP 15834593.4.

Japanese Office Action dated Jul. 13, 2020 issued in JP 2018-501208.

European Extended Search Report dated Sep. 7, 2020 issued in EP 18744685.1.

Drummond, et al. (1996) "Thoracic impedance used for measuring chest wall movement in postoperative patients," *British Journal of Anaesthesia,* 77: 327-332.

Hovey, et al. (2006) "The Guide to Magnetic Stimulation," *The Magstim Company Ltd,* 45 pages.

Kondo, et al. (1997) "Laser monitoring of chest wall displacement," *Eur Respir J.*, 10: 1865-1869.

Niu et al., (2018) "A Proof-of-Concept Study of Transcutaneous Magnetic Spinal Cord Stimulation for Neurogenic Bladder," *Scientific Reports,* 8: 12549 (12 pages).

Szava et al., (Jan. 2011) "Transcutaneous electrical spinal cord stimulation: Biophysics of a new rehabilitation method after spinal cord injury", ISBN: 978-3-639-34154-6.

U.S. Office Action dated Nov. 24, 2020 issued in U.S. Appl. No. 16/200,467.

U.S. Office Action dated Feb. 10, 2021 issued in U.S. Appl. No. 15/975,678.

U.S. Final Office Action dated Nov. 20, 2020 issued in U.S. Appl. No. 15/740,323.

U.S. Office Action dated Mar. 29, 2021 issued in U.S. Appl. No. 15/740,323.

U.S. Notice of Allowance dated Apr. 27, 2021 issued in U.S. Appl. No. 15/344,381.

Australian Examination report No. 1 dated Dec. 21, 2020 issued in AU 2020200152.

Canadian Office Action dated Nov. 27, 2020 issued in CA 2,925,754.

European Extended Search Report dated Jan. 22, 2021 issued in EP 20175385.2.

Canadian 2nd Office Action dated Apr. 9, 2021 issued in CA 2,906,779.

Chinese First Office Action dated Jan. 6, 2021 issued in CN 201680058067.8.

Japanese 2nd Office Action dated Mar. 22, 2021 issued in JP 2018-501208.

PCT International Preliminary Report on Patentability and Written Opinion dated Feb. 23, 2021 issued in PCT/US2019/047777.

PCT International Preliminary Report on Patentability and Written Opinion dated Feb. 23, 2021 issued in PCT/US2019/047551.

PCT International Search Report and Written Opinion dated Oct. 14, 2020 issued in PCT/US2020/033830.

U.S. Notice of Allowance dated May 19, 2021 issued in U.S. Appl. No. 16/200,467.

U.S. Final Office Action dated Jul. 20, 2021 issued in U.S. Appl. No. 15/975,678.

U.S. Office Action dated Aug. 6, 2021 issued in U.S. Appl. No. 15/750,499.

U.S. Office Action dated May 12, 2021 issued in U.S. Appl. No. 16/615,765.

European Extended Search Report dated Aug. 17, 2021 issued in EP 21166801.7.

\* cited by examiner

CONCERTED USE OF NONINVASIVE NEUROMODULATION DEVICE WITH EXOSKELETON TO ENABLE VOLUNTARY MOVEMENT AND GREATER MUSCLE ACTIVATION WHEN STEPPING IN A CHRONICALLY PARALYZED SUBJECT

CROSS-REFERENCE TO RELATED APPLICATIONS

This application is a US 371 National Phase of PCT/US2016/049129, filed on Aug. 26, 2016, which claims benefit of and priority to U.S. Ser. No. 62/210,070, filed on Aug. 26, 2015, both of which are incorporated herein by reference in their entirety for all purposes.

STATEMENT OF GOVERNMENTAL SUPPORT

[Not Applicable]

BACKGROUND

Non-invasive neurostimulator or neuromodulation devices have been described in the art and are used to deliver therapy to patients to treat a variety of symptoms or conditions such as post traumatic pain, chronic pain, neuropathy, neuralgia, epilepsy, and tremor. Little progress has been made in the prior art of using a neuromodulator for restoration function to the damaged nervous system. With regards to locomotion, neuronal circuitries have shown levels of activation attributable to electromagnetic spinal cord stimulation (Gerasimenko et al. (2010) *J. Neurosci.* 30: 3700-3708). Additionally, it has been shown that a traditional technique to apply transcutaneous electrical spinal cord stimulation (tSCS) can facilitate locomotor output in spinal cord injury patients. Most recently, a non-invasive transcutaneous electrical stimulation strategy has been shown to effectively modulate spinal cord physiology enabling restoration and/or enhancement of voluntary motor controlled stepping.

Robotic exoskeleton therapy as applied to rehabilitation has been described in the art as a wearable, electronic modulator of movement that otherwise would have been unfit for functional use. Robotic therapy has been tested as a method to improve locomotion in paralyzed subjects.

SUMMARY

In various embodiments the methods described herein provide means and systems for the facilitation of movement using a bionic exoskeleton designed to enable individuals with lower extremity weakness to stand and step over ground as a compliment to chronic stimulation of any and all components of the nervous system with a rechargeable neuromodulator that delivers an electric charge non-invasively through conductive electrodes. The neuromodulator electrodes containing single or multiple arrays may be placed on the skin overlying the spinal cord, spinal nerve(s), nerve root(s), ganglia, peripheral nerve(s), brainstem or target areas such as skeletal muscles.

Stimulation and control parameters of the stimulator can be adjusted to levels that are safe and efficacious using parameters chosen to target specific neural components, or end organs and customized to each patient based on response to evaluation and testing. The neuromodulator can also have a variable activation control for providing stimulation either intermittently or continuously, allowing for adjustments to frequency, amplitude, and duration.

Various embodiments contemplated herein may include, but need not be limited to, one or more of the following:

Embodiment 1

A method of stimulating or improving postural and/or locomotor activity and/or postural or locomotor strength, and/or reaching or grasping, and/or fine motor control of a hand in a human subject having a spinal cord injury, a brain injury, and/or a neurodegenerative pathology, said method comprising:
  applying transcutaneous stimulation to the spinal cord, brainstem or brain, or sacral nerves of said subject thereby activating neural networks of the spinal cord; and
  utilizing a powered orthotic exoskeletal system to expose said subject to relevant postural, and/or weight bearing, and/or locomotor and/or proprioceptive signals;
  whereby the combination of transcutaneous stimulation and exoskeletal system use enhances postural and/or locomotor activity and/or postural or locomotor strength, and/or reaching or grasping, and/or fine motor control of a hand.

Embodiment 2

The method according of embodiment 1, wherein the combination of said transcutaneous stimulation and exoskeletal system modulates in real time the electrophysiological properties of spinal circuits in said subject so they are activated by proprioceptive information derived from the desired region of the subject.

Embodiment 3

The method according to any one of embodiments 1-2, wherein said method enhances autonomic functions in said subject.

Embodiment 4

The method of embodiment 3, wherein said autonomic functions comprise one or more functions selected from the group consisting of comprise cardiovascular function, and thermoregulation.

Embodiment 5

The method of embodiment 3, wherein said autonomic functions comprise one or more functions selected from the group consisting of bladder function, bowel function, sexual function, digestive function, metabolic function, and pulmonary function.

Embodiment 6

The method according to any one of embodiments 1-5, wherein the enhancement provided by the combination of transcutaneous stimulation and exoskeletal system is synergistic.

Embodiment 7

The method according to any one of embodiments 1-6, wherein said exoskeletal system partially or fully controls movement of a leg, arm, and/or hand.

Embodiment 8

The method according to any one of embodiments 1-7, wherein said exoskeletal system fully controls a load bearing positional change in the region of the subject where locomotor activity is to be facilitated.

Embodiment 9

The method according to any one of embodiments 1-7, wherein said exoskeletal system partially controls a load bearing positional change in the region of the subject where locomotor activity is to be facilitated.

Embodiment 10

The method according to any one of embodiments 1-7, wherein said exoskeletal system provides variable assistance where corrective assistance is provided based on the extent of deviation by the human from a healthy and/or predetermined motion and/or by the variation in resistance to a load provided by the subject.

Embodiment 11

The method according to any one of embodiments 1-10, wherein said exoskeletal system provides assistance to said subject in standing.

Embodiment 12

The method according to any one of embodiments 1-11, wherein said exoskeletal system provides assistance to said subject in rising to standing from a seated or reclining position.

Embodiment 13

The method according to any one of embodiments 1-12, wherein said exoskeletal system provides assistance to said subject in stepping.

Embodiment 14

The method according to any one of embodiments 1-13, wherein said exoskeletal system provides assistance to said subject in sitting down or laying down.

Embodiment 15

The method according to any one of embodiments 1-14, wherein said exoskeletal system provides assistance to said subject in stabilizing sitting or standing posture.

Embodiment 16

The method according to any one of embodiments 1-15, wherein said exoskeletal system provides assistance to said subject in reaching.

Embodiment 17

The method according to any one of embodiments 1-16, wherein said exoskeletal system provides assistance to said subject in grasping.

Embodiment 18

The method according to any one of embodiments 1-17, wherein said transcutaneous stimulation is at a frequency ranging from about 0.5 Hz, or from about 1 Hz, or from about 3 Hz, or from abut 5 Hz up to about 1,000 Hz, or up to about 500 Hz, or up to about 100 Hz, or up to about 80 Hz, or up to about 40 Hz, or from about 3 Hz or from about 5 Hz up to about 80 Hz, or from about 5 Hz up to about 30 Hz, or up to about 40 Hz, or up to about 50 Hz.

Embodiment 19

The method according to any one of embodiments 1-18, wherein said transcutaneous stimulation is at an amplitude ranging from 10 mA to about 500 mA, or up to about 300 mA, or up to about 150 mA, or from about 20 mA to about 300 mA, or up to about 50 mA or up to about 100 mA, or from about 20 mA or from about 30 mA, or from about 40 mA to about 50 mA, or to about 60 mA, or to about 70 mA or to about 80 mA.

Embodiment 20

The method according to any one of embodiments 1-19, wherein said transcutaneous stimulation pulse width ranges from about 100 μs up to about 200 ms, or from about 100 μs, or from about 150 μs, or from about 200 μs, up to about 900 μs, or up to about 800 μs, or up to about 700 μs, or up to about 600 μs, or up to about 500 μs, or up to about 450 μs, or from about 1 ms, or from about 2 ms, or from about 5 ms, or from about 10 ms, or from about 20 ms, or from about 50 ms up to about 200 ms, or up to about 150 ms, or up to about 100 ms, or up to about 80 ms, or up to about 60 ms.

Embodiment 21

The method according to any one of embodiments 1-20, wherein said transcutaneous stimulation is superimposed on a high frequency carrier signal.

Embodiment 22

The method of embodiment 21, wherein said high frequency carrier signal ranges from 3 kHz, or about 5 kHz, or about 8 kHz up to about 100 kHz, or up to about 80 kHz, or up to about 50 kHz, or up to about 40 kHz, or up to about 30 kHz, or up to about 20 kHz, or up to about 15 kHz.

Embodiment 23

The method of embodiment 22, wherein said high frequency carrier signal is about 10 kHz.

Embodiment 24

The method according to any one of embodiments 21-23, wherein said carrier frequency amplitude ranges from about 30 mA, or about 40 mA, or about 50 mA, or about 60 mA, or about 70 mA, or about 80 mA up to about 500 mA, or up to about 300 mA, or up to about 200 mA, or up to about 150 mA.

Embodiment 25

The method according to any one of embodiments 1-24, wherein said transcutaneous stimulation is at a frequency and amplitude sufficient to stimulate and/or to improve postural and/or locomotor activity and/or postural or locomotor strength.

Embodiment 26

The method according to any one of embodiments 1-24, wherein said transcutaneous stimulation is at a frequency and amplitude sufficient to stimulate and/or improve reaching and/or grasping and/or fine motor control of a hand.

Embodiment 27

The method according to any one of embodiments 1-26, wherein said transcutaneous stimulation is provided in a monopolar configuration.

Embodiment 28

The method according to any one of embodiments 1-26, wherein said transcutaneous stimulation is provided in a bipolar configuration.

Embodiment 29

The method according to any one of embodiments 1-28, wherein said transcutaneous stimulation is provided in a monophasic configuration.

Embodiment 30

The method according to any one of embodiments 1-28, wherein said transcutaneous stimulation is provided in a biphasic configuration.

Embodiment 31

The method according to any one of embodiments 1-30, wherein said transcutaneous stimulation comprises tonic stimulation.

Embodiment 32

The method according to any one of embodiments 1-31, wherein said transcutaneous stimulation comprises stimulation of a single region of the spinal cord.

Embodiment 33

The method according to any one of embodiments 1-31, wherein said transcutaneous stimulation comprises simultaneous or sequential stimulation of different spinal cord regions.

Embodiment 34

The method according to any one of embodiments 1-33, wherein said transcutaneous stimulation is applied on the skin surface over the cervical spine or a region thereof and/or over the thoracic spine or a region thereof, and/or over the lumbosacral spine or a region thereof.

Embodiment 35

The method according to any one of embodiments 1-34, wherein said transcutaneous stimulation is applied on the skin surface over a region of the spinal cord that controls the lower limbs to stimulate or improve postural and/or locomotor activity and/or postural or locomotor strength.

Embodiment 36

The method according to any one of embodiments 1-31, and 33-35, wherein said transcutaneous stimulation is applied on the skin surface over a region of the thoracic spinal cord and over a region of the lumbar spinal cord.

Embodiment 37

The method according to any one of embodiments 35-36, wherein said transcutaneous stimulation is applied on the skin surface over a region comprising T11.

Embodiment 38

The method according to any one of embodiments 35-37, wherein said transcutaneous stimulation is applied on the skin surface over a region comprising the coccygeal nerve Co1.

Embodiment 39

The method according to any one of embodiments 1-34, wherein said transcutaneous stimulation is applied on the skin surface over a region of the spinal cord that controls the upper limbs to improve reaching and/or grasping and/or to improve improving motor control and/or strength in a hand and/or upper limb of a subject with a neuromotor disorder affecting motor control of the hand and/or upper limb.

Embodiment 40

The method of embodiment 39, wherein said transcutaneous stimulation is applied on the skin surface over a region comprising the cervical spinal cord.

Embodiment 41

The method according to any one of embodiments 1-40, wherein the transcutaneous stimulation is under control of the subject.

Embodiment 42

The method according to any one of embodiments 1-41, wherein said exoskeletal system is under control of the subject.

Embodiment 43

The method according to any one of embodiments 1-42, wherein said exoskeletal system comprises a wearable powered orthotic system.

Embodiment 44

The method of embodiment 43, wherein said powered orthotic system comprises: a torso portion configurable to be coupled to an upper body of a person; and a lower limb orthotic component configured to provide assistance in locomotion of a lower limb and/or an upper limb powered orthotic component configured to provide assistance in locomotion of an upper limb; and a plurality of sensors for monitoring positions of said lower limb orthotic component and/or said upper limb orthotic component; and a controller configured to control assistance provided by said lower limb orthotic component and/or configured to control assistance provided by said upper limb orthotic component.

Embodiment 45

The method of embodiment 44, wherein said exoskeletal system comprises a lower limb orthotic component comprising at least one leg support configurable to be coupled to a first lower limb of the person, with the at least one leg support including at least a thigh link rotatably connected to the torso portion at a hip joint, and a shank link rotatably connected to the thigh link at a knee joint; a first lower limb actuator for controlling motion of said hip joint; and a second lower limb actuator for controlling motion of said knee joint.

Embodiment 46

The method of embodiment 45, wherein said controller is configured to control the first and second lower limb actuators with adaptive, variable levels of assistance in response to signals from the plurality of sensors.

Embodiment 47

The method according to any one of embodiments 44-46, wherein said exoskeletal system comprises an upper limb orthotic component comprising at least one arm support configured to be coupled to a first upper limb of the person, with the at least one arm support including at least an upper arm (brachium) link rotatably connected to the torso portion at a shoulder joint, and a forearm (antebrachium) link rotatably connected to the upper arm link at an elbow; a first upper limb actuator for controlling motion of said shoulder joint; and a second upper limb actuator for controlling motion of said elbow joint.

Embodiment 48

The method of embodiment 47, wherein said controller is configured to control the first and second upper limb actuators with adaptive, variable levels of assistance in response to signals from the plurality of sensors.

Embodiment 49

The method according to any one of embodiments 1-48, wherein said exoskeletal system is configured to perform gait functions for the subject based on a predetermined level of assistance.

Embodiment 50

The method according to any one of embodiments 1-48, wherein said exoskeletal system is configured to perform gait functions where the level of assistance is adaptively varied based on performance of the subject.

Embodiment 51

The method according to any one of embodiments 1-48, wherein said exoskeletal system is configured to perform arm movements for the wearer based on a predetermined level of assistance.

Embodiment 52

The method according to any one of embodiments 1-48, wherein said exoskeletal system is configured to perform arm movements where the level of assistance is adaptively varied based on performance of the subject.

Embodiment 53

The method according to any one of embodiments 43-52, wherein said controller is integrated into said exoskeleton system.

Embodiment 54

The method according to any one of embodiments 43-52, wherein said controller is external to said exoskeleton.

Embodiment 55

The method according to any one of embodiments 43-54, wherein a power source is integrated into said exoskeletal system.

Embodiment 56

The method according to any one of embodiments 43-54, wherein a power source is external to said exoskeleton system.

Embodiment 57

The method according to any one of embodiments 55-56, wherein the same power source provides power for both operation of the exoskeletal system and for said transcutaneous stimulation.

Embodiment 58

The method according to any one of embodiments 55-56, wherein different power sources provide power for both operation of the exoskeletal system and for said transcutaneous stimulation.

Embodiment 59

The method of embodiment 43, wherein said exoskeleton comprises an EKSO GT™ exoskeleton.

Embodiment 60

The method according to any one of embodiments 1-58, wherein said subject is administered at least one neuromodulatory drug.

Embodiment 61

The method of embodiment 60, wherein said subject is administered at least one monoaminergic agonist.

Embodiment 62

The method of embodiment 61, wherein said at least one monoaminergic agonist comprises an agent selected from

9 the group consisting of a serotonergic drug, a dopaminergic drug, a noradrenergic drug, a GABAergic drug, and a glycinergic drug.

Embodiment 63

The method of embodiment 61, wherein said agent is selected from the group consisting of 8-hydroxy-2-(di-n-propylamino)tetralin (8-OH-DPAT), 4-(benzodioxan-5-yl) 1-(indan-2-yl)piperazine (S15535), N-{2-[4-(2-methoxy-phenyl)-1-piperazinyl]ethyl}-N-(2-pyridinyl)cyclo-hexanecarboxamide (WAY 100.635), Quipazine, Ketanserin, 4-amino-(6-chloro-2-pyridyl)-1 piperidine hydrochloride (SR 57227A), Ondanesetron, Buspirone, Methoxamine, Prazosin, Clonidine, Yohimbine, 6-chloro-1-phenyl-2,3,4,5-tetrahydro-1H-3-benzazepine-7,8-diol (SKF-81297), 7-chloro-3-methyl-1-phenyl-1,2,4,5-tetrahydro-3-benzazepin-8-ol (SCH-23390), Quinpirole, and Eticlopride.

Embodiment 64

The method of embodiment 61, wherein said monoaminergic agonist is buspirone.

Embodiment 65

The method of embodiment 60, wherein said neuromodulatory drug is a molecule that activates (e.g., selectively activates) an α2c adrenergic receptor subtype and/or that blocks (e.g., selectively blocks) blocking an α2a adrenergic receptor subtype.

Embodiment 66

The method of embodiment 65, wherein said molecule that activates an α2c adrenergic receptor subtype is 2-[(4, 5-Dihydro-1H-imidazol-2-yl)methyl]-2,3-dihydro-1-methyl-1H-isoindole (BRL-44408).

Embodiment 67

The method of embodiment 65, wherein said molecule that activates an α2c adrenergic receptor subtype is (R)-3-nitrobiphenyline and/or a compound according to the formula:

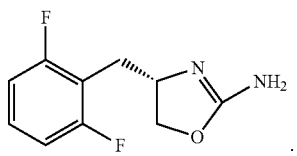

Embodiment 68

The method of embodiment 65, wherein said agonist is Clonidine.

Embodiment 69

The method of embodiment 65, wherein said neuromodulatory drug further comprises a 5-HT1 and/or a 5-HT7 serotonergic agonist.

Embodiment 70

The method according to any one of embodiments 1-69, wherein said subject has a spinal cord injury.

Embodiment 71

The method of embodiment 70, wherein said spinal cord injury is clinically classified as motor complete.

Embodiment 72

The method according to any one of embodiments 1-70, wherein said spinal cord injury is clinically classified as motor incomplete.

Embodiment 73

The method according to any one of embodiments 1-69, wherein said subject has an ischemic brain injury.

Embodiment 74

The method of embodiment 73, wherein said ischemic brain injury is brain injury from stroke or acute trauma.

Embodiment 75

The method according to any one of embodiments 1-69, wherein said subject has a neurodegenerative pathology.

Embodiment 76

The method of embodiment 75, wherein said neurodegenerative pathology is associated with a condition selected from the group consisting of stroke, Parkinson's disease, Huntington's disease, Alzheimer's disease, amyotrophic lateral sclerosis (ALS), primary lateral sclerosis (PLS), dystonia, and cerebral palsy.

Embodiment 77

A system for said system comprising:
a transcutaneous electrical stimulator; and
an orthotic exoskeleton.

Embodiment 78

The system of embodiment 77, wherein said orthotic exoskeleton is a powered orthotic exoskeleton.

Embodiment 79

The system according to any one of embodiments 77-78, wherein said orthotic exoskeleton is configured to manipulate a limb or region of a human subject and/or to apply postural and/or weight bearing loads to said subject.

Embodiment 80

The system according to any one of embodiments 77-79, wherein said system is configured to perform a method according to any one of embodiments 1-40.

Embodiment 81

The system according to any one of embodiments 77-80, wherein the combination of said transcutaneous stimulation and exoskeletal system modulates in real time the electrophysiological properties of spinal circuits in said subject so they are activated by proprioceptive information derived from the desired region of the subject.

Embodiment 82

The system according to any one of embodiments 77-81, wherein said exoskeletal system is configured to partially or fully control movement of a leg, arm, and/or hand.

Embodiment 83

The system according to any one of embodiments 77-81, wherein said exoskeletal system is configured to partially control a load bearing positional change in the region of the subject where locomotor activity is to be facilitated.

Embodiment 84

The system according to any one of embodiments 77-81, wherein said exoskeletal system is configured to fully control a load bearing positional change in the region of the subject where locomotor activity is to be facilitated.

Embodiment 85

The system according to any one of embodiments 77-81, wherein said exoskeletal system is configured to provide variable assistance where corrective assistance is provided based on the extent of deviation by the human from a healthy and/or predetermined motion and/or by the variation in resistance to a load provided by the subject.

Embodiment 86

The system according to any one of embodiments 77-85, wherein said exoskeletal system is configured to provide assistance to said subject in standing.

Embodiment 87

The system according to any one of embodiments 77-86, wherein said exoskeletal system is configured to provide assistance to said subject in rising to standing from a seated or reclining position.

Embodiment 88

The system according to any one of embodiments 77-87, wherein said exoskeletal system is configured to provide assistance to said subject in stepping.

Embodiment 89

The system according to any one of embodiments 77-88, wherein said exoskeletal system is configured to provide assistance to said subject in sitting down or laying down.

Embodiment 90

The system according to any one of embodiments 77-89, wherein said exoskeletal system is configured to provide assistance to said subject in stabilizing sitting or standing posture.

Embodiment 91

The system according to any one of embodiments 77-90, wherein said exoskeletal system is configured to provide assistance to said subject in reaching.

Embodiment 92

The system according to any one of embodiments 77-91, wherein said exoskeletal system is configured to provide assistance to said subject in grasping.

Embodiment 93

The system according to any one of embodiments 77-92, wherein said transcutaneous electrical stimulator is configured to provide transcutaneous stimulation at a frequency ranging from about 0.5 Hz or from about 3 Hz, or from about 5 Hz, or from about 10 Hz up to about 50 kHz, or up to about 30 kHz, or up to about 20 kHz, or up to about 10 kHz, or up to about 1,000 Hz, or up to about 500 Hz, or up to about 100 Hz, or up to about 80 Hz, or up to about 40 Hz, or from about 3 Hz or from about 5 Hz up to about 80 Hz, or from about 5 Hz up to about 30 Hz, or up to about 40 Hz, or up to about 50 Hz.

Embodiment 94

The system according to any one of embodiments 77-93, wherein said transcutaneous electrical stimulator is configured to provide transcutaneous stimulation at an amplitude ranging from 10 mA to about 500 mA, or up to about 300 mA, or up to about 150 mA, or from about 20 mA to about 300 mA, or up to about 50 mA or up to about 100 mA, or from about 20 mA or from about 30 mA, or from about 40 mA to about 50 mA, or to about 60 mA, or to about 70 mA or to about 80 mA.

Embodiment 95

The system according to any one of embodiments 77-94, wherein said transcutaneous electrical stimulator is configured to provide transcutaneous stimulation having a pulse width that ranges from about 100 μs up to about 200 ms, or from about 100 μs, or from about 150 μs, or from about 200 μs, up to about 900 μs, or up to about 800 μs, or up to about 700 μs, or up to about 600 μs, or up to about 500 μs, or up to about 450 μs, or from about 1 ms, or from about 2 ms, or from about 5 ms, or from about 10 ms, or from about 20 ms, or from about 50 ms up to about 200 ms, or up to about 150 ms, or up to about 100 ms, or up to about 80 ms, or up to about 60 ms.

Embodiment 96

The system according to any one of embodiments 77-95, wherein said transcutaneous electrical stimulator is configured to provide transcutaneous stimulation superimposed on a high frequency carrier signal.

Embodiment 97

The system of embodiment 96, wherein said high frequency carrier signal ranges from 3 kHz, or about 5 kHz, or about 8 kHz up to about 100 kHz, or up to about 80 kHz, or up to about 50 kHz, or up to about 40 kHz, or up to about 30 kHz, or up to about 20 kHz, or up to about 15 kHz.

Embodiment 98

The system of embodiment 97, wherein said high frequency carrier signal is about 10 kHz.

Embodiment 99

The system according to any one of embodiments 96-98, wherein said transcutaneous electrical stimulator is configured to provide transcutaneous stimulation with a carrier frequency having an amplitude that ranges from about 30 mA, or about 40 mA, or about 50 mA, or about 60 mA, or about 70 mA, or about 80 mA up to about 500 mA, or up to about 300 mA, or up to about 200 mA, or up to about 150 mA.

Embodiment 100

The system according to any one of embodiments 77-99, wherein said transcutaneous electrical stimulator is configured to provide transcutaneous stimulation at a frequency and amplitude sufficient to stimulate and/or to improve postural and/or locomotor activity and/or postural or locomotor strength.

Embodiment 101

The system according to any one of embodiments 77-99, wherein said transcutaneous electrical stimulator is configured to provide transcutaneous stimulation at a frequency and amplitude sufficient to stimulate and/or improve reaching and/or grasping and/or fine motor control of a hand.

Embodiment 102

The system according to any one of embodiments 77-101, wherein said transcutaneous electrical stimulator is configured to provide transcutaneous stimulation in a monopolar configuration.

Embodiment 103

The system according to any one of embodiments 77-101, wherein said transcutaneous electrical stimulator is configured to provide transcutaneous stimulation in a bipolar configuration.

Embodiment 104

The system according to any one of embodiments 77-103, wherein said transcutaneous electrical stimulator is configured to provide transcutaneous stimulation in a monophasic configuration.

Embodiment 105

The system according to any one of embodiments 77-103, wherein said transcutaneous electrical stimulator is configured to provide transcutaneous stimulation in a biphasic configuration.

Embodiment 106

The system according to any one of embodiments 77-105, wherein said transcutaneous electrical stimulator is configured to provide tonic stimulation.

Embodiment 107

The system according to any one of embodiments 77-105, wherein said transcutaneous electrical stimulator is configured to provide intermittent stimulation.

Embodiment 108

The system according to any one of embodiments 77-106, wherein said transcutaneous electrical stimulator is configured to provide transcutaneous stimulation of a single region of the spinal cord.

Embodiment 109

The system according to any one of embodiments 77-106, wherein said transcutaneous electrical stimulator is configured to provide transcutaneous stimulation simultaneous or sequentially to different spinal cord regions.

Embodiment 110

The system according to any one of embodiments 77-109, wherein said transcutaneous electrical stimulator is configured to provide transcutaneous stimulation on the skin surface over the cervical spine or a region thereof and/or over the thoracic spine or a region thereof, and/or over the lumbosacral spine or a region thereof.

Embodiment 111

The system according to any one of embodiments 77-110, wherein said transcutaneous electrical stimulator is configured to provide transcutaneous stimulation on the skin surface over a region of the spinal cord that controls the lower limbs upper limbs to stimulate or improve postural and/or locomotor activity and/or postural or locomotor strength.

Embodiment 112

The system according to any one of embodiments 77-107, and 109-111, wherein said transcutaneous electrical stimulator is configured to provide transcutaneous stimulation on the skin surface over a region of the thoracic spinal cord and over a region of the lumbar spinal cord.

Embodiment 113

The system according to any one of embodiments 111-112, wherein said transcutaneous electrical stimulator is configured to provide transcutaneous stimulation on the skin surface over a region comprising T11.

Embodiment 114

The system according to any one of embodiments 111-113, wherein said transcutaneous electrical stimulator is configured to provide transcutaneous stimulation on the skin surface over a region comprising the coccygeal nerve Co1.

Embodiment 115

The system according to any one of embodiments 77-110, wherein said transcutaneous electrical stimulator is configured to provide transcutaneous stimulation on the skin surface over a region of the spinal cord that controls the upper limbs to improve reaching and/or grasping and/or to improve improving motor control and/or strength in a hand and/or upper limb of a subject with a neuromotor disorder affecting motor control of the hand and/or upper limb.

Embodiment 116

The system of embodiment 115, wherein said transcutaneous electrical stimulator is configured to provide transcutaneous stimulation on the skin surface over a region comprising the cervical spinal cord.

Embodiment 117

The system according to any one of embodiments 77-116, wherein the transcutaneous electrical stimulator is configured to provide transcutaneous stimulation under control of the subject.

Embodiment 118

The system according to any one of embodiments 77-117, wherein said exoskeletal system is configured to operate under control of the subject.

Embodiment 119

The system according to any one of embodiments 77-117, wherein said exoskeletal system is configured to operate under control of a person other than the subject.

Embodiment 120

The system according to any one of embodiments 77-118, wherein said exoskeletal system comprises a wearable orthotic system.

Embodiment 121

The system of embodiment 120, wherein said exoskeletal system comprises a wearable unpowered orthotic system.

Embodiment 122

The system of embodiment 120, wherein said exoskeletal system comprises a wearable powered orthotic system.

Embodiment 123

The system of embodiment 122, wherein said powered orthotic system comprises: a torso portion configurable to be coupled to an upper body of a person; and a powered lower limb orthotic component configured to provide assistance in locomotion of a lower limb and/or an upper limb powered orthotic component configured to provide assistance in locomotion of an upper limb; and a plurality of sensors for monitoring positions of said lower limb orthotic component and/or said upper limb orthotic component; and a controller configured to control assistance provided by said lower limb orthotic component and/or configured to control assistance provided by said upper limb orthotic component.

Embodiment 124

The system of embodiment 123, wherein said exoskeletal system comprises a lower limb orthotic component comprising:
  at least one leg support configured to be coupled to a first lower limb of the person, with the at least one leg support including at least a thigh link rotatably connected to the torso portion at a hip joint, and a shank link rotatably connected to the thigh link at a knee joint;
  a first lower limb actuator for controlling motion of said hip joint; and
  a second lower limb actuator for controlling motion of said knee joint.

Embodiment 125

The system of embodiment 124, wherein said controller is configured to control the first and second lower limb actuators with adaptive, variable levels of assistance in response to signals from the plurality of sensors.

Embodiment 126

The system according to any one of embodiments 123-125, wherein said exoskeleton system comprises:
  an upper limb orthotic component comprising at least one arm support configurable to be coupled to a first upper limb of the person, with the at least one arm support including at least an upper arm (brachium) link rotatably connected to the torso portion at a shoulder joint, and a forearm (antebrachium) link rotatably connected to the upper arm link at an elbow;
  a first upper limb actuator for controlling motion of said shoulder joint; and
  a second upper limb actuator for controlling motion of said elbow joint.

Embodiment 127

The system of embodiment 126, wherein said controller is configured to control the first and second upper limb actuators with adaptive, variable levels of assistance in response to signals from the plurality of sensors.

Embodiment 128

The system according to any one of embodiments 77-127, wherein said exoskeletal system is configured to perform gait functions for the subject based on a predetermined level of assistance.

Embodiment 129

The system according to any one of embodiments 77-127, wherein said exoskeletal system is configured to perform gait functions where the level of assistance is adaptively varied based on performance of the subject.

Embodiment 130

The system according to any one of embodiments 77-127, wherein said exoskeletal system is configured to perform arm movements for the wearer based on a predetermined level of assistance.

Embodiment 131

The system according to any one of embodiments 77-127, wherein said exoskeletal system is configured to perform arm movements where the level of assistance is adaptively varied based on performance of the subject.

Embodiment 132

The system according to any one of embodiments 120-131, wherein said controller is integrated into said exoskeleton system.

Embodiment 133

The system according to any one of embodiments 120-131, wherein said controller is external to said exoskeleton.

Embodiment 134

The system according to any one of embodiments 132-133, wherein said controller controls said transcutaneous electrical stimulator in addition to said exoskeleton.

Embodiment 135

The system according to any one of embodiments 77-134, wherein the exoskeleton and stimulator are configured to adjust transcutaneous stimulation patterns based on feedback from the exoskeleton.

Embodiment 136

The system according to any one of embodiments 120-135, wherein a power source is integrated into said exoskeletal system.

Embodiment 137

The system according to any one of embodiments 120-135, wherein a power source is external to said exoskeleton system.

Embodiment 138

The system according to any one of embodiments 136-137, wherein the same power source provides power for both operation of the exoskeletal system and for said transcutaneous stimulation.

Embodiment 139

The system according to any one of embodiments 136-137, wherein different power sources provide power for both operation of the exoskeletal system and for said transcutaneous stimulation.

Embodiment 140

The system of embodiment 77, wherein said exoskeleton comprises an EKSO GT™ exoskeleton.

BRIEF DESCRIPTION OF THE DRAWINGS

FIG. 5, panel B: Mean±SD assistance provided by the EKSO during stepping under different conditions. FIG. 5, panel C: Mean±SD current drawn by the knee motor while stepping in the EKSO under different conditions.

DETAILED DESCRIPTION

Figure 1:
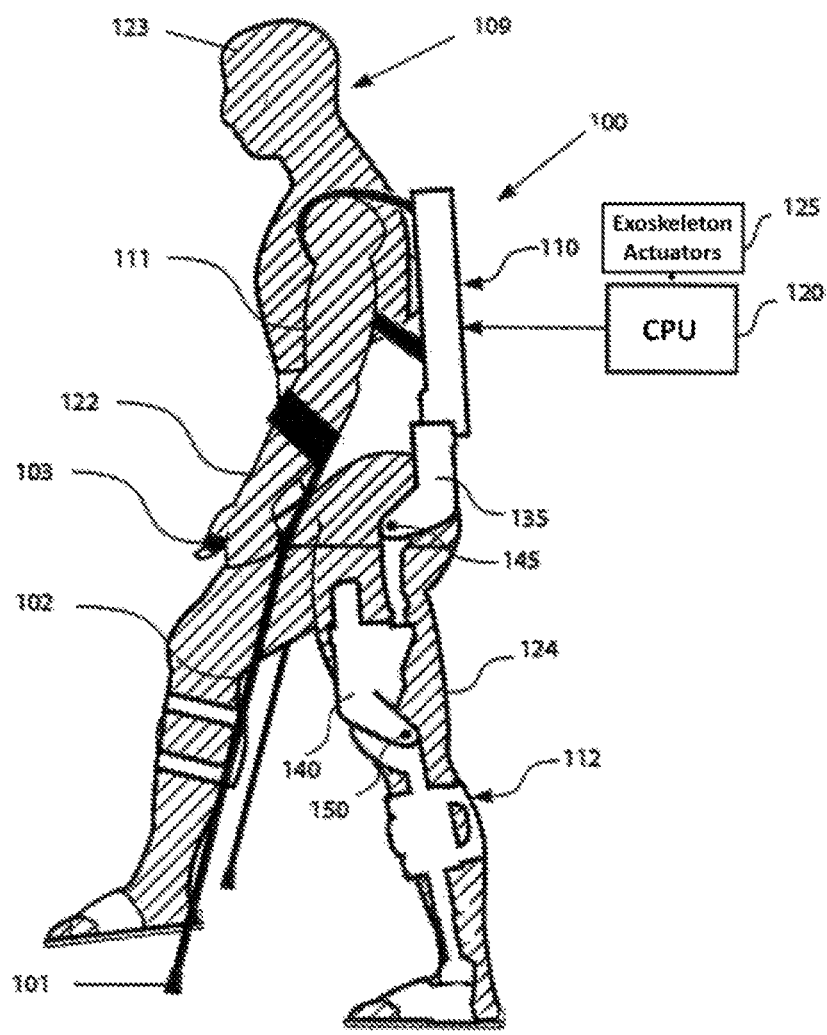
FIG. 1 schematically illustrates a figure of a person wearing an exoskeleton as described in U.S. Patent Pub. No: 2016/0030201 A1.

Experiments were performed to determine whether coordinated voluntary movement of the lower limbs could be regained in an individual having been completely paralyzed (>4 yr) and completely absent of vision (>15 yr) using a novel strategy—transcutaneous spinal cord stimulation at selected sites over the spinal vertebrae with just one week of training. Experiments were also performed to determine whether this stimulation strategy could facilitate stepping assisted by an exoskeleton (EKSO, EKSO Bionics) that is designed so that the subject can voluntarily complement the work being performed by the exoskeleton. It was discovered that that spinal cord stimulation enhanced the level of effort that the subject could generate while stepping in the exoskeleton. In addition, stimulation improved the coordination patterns of the lower limb muscles resulting in a more continuous, smooth stepping motion in the exoskeleton. These stepping sessions in the presence of stimulation were accompanied by greater cardiac responses and sweating than could be attained without the stimulation. Based on the data from this case study it is believed that there is considerable potential for positive synergistic effects after complete paralysis by combining the overground stepping in an exoskeleton, a novel transcutaneous spinal cord stimulation paradigm, and daily training.

More generally, in view of the experiments described herein, it is believed that exoskeletal orthotic systems can be used in combination with transcutaneous stimulation of regions of the spinal cord to stimulate and/or improve postural and/or locomotor activity and/or postural or locomotor strength and/or reaching or grasping, and/or fine motor control of a hand in a human subject having a spinal cord injury, a brain injury, and/or a neurodegenerative pathology. In various embodiments the methods typically involve applying transcutaneous stimulation to the spinal cord, brainstem or brain, or sacral nerves of the subject thereby activating neural networks of the spinal cord; and utilizing a powered orthotic exoskeletal system to expose the subject to relevant postural, and/or weight bearing, and/or locomotor and/or motor proprioceptive signals. It is believed the combination of transcutaneous stimulation and exoskeletal system use enhances postural and/or locomotor activity and/or postural or locomotor strength, and/or reaching or grasping, and/or fine motor control of a hand. In certain embodiments the combination of said transcutaneous stimulation and exoskeletal system modulates in real time the electrophysiological properties of spinal circuits in said subject so they are activated by proprioceptive information derived from the desired region of the subject. In certain embodiments the methods enhance autonomic functions (e.g., cardiovascular function, thermoregulation, etc.) in the subject. In certain embodiments the enhancement provided by the combination of transcutaneous stimulation and exoskeletal system is synergistic.

In certain embodiments systems provided for use in the methods described herein. In certain embodiments the system(s) comprise a transcutaneous electrical stimulator; and a powered orthotic exoskeleton. In certain embodiments the system(s) comprise a transcutaneous electrical stimulator; and a non-powered orthotic exoskeleton. In certain embodiments the transcutaneous stimulator is integrated into the exoskeleton, while in other embodiments the transcutaneous stimulator is provided as a separate component. In certain embodiments the exoskeleton comprises a controller and the controller can additionally control the transcutaneous electrical stimulator. In certain embodiments the transcutaneous stimulator has a controller and the controller can additionally control the exoskeleton. In certain embodiments the orthotic exoskeletal system and the stimulator are configured to create a closed loop system. In certain embodiments the exoskeleton also contains an integrated power source and in certain embodiments that power source can also be used to power the transcutaneous stimulator. In other embodiments, the transcutaneous stimulator can utilize a different power source than the exoskeleton. In certain embodiments the stimulation may be applied using an implantable stimulator system with electrode array as described in U.S. Pat. No. 9,409,023 B2.

Exoskeletons for Use in the Methods and Systems Described Herein.

As explained above, in various embodiments, exoskeletal systems, especially robotic powered orthotic exoskeletal systems are used in combination with transcutaneous electrical stimulation of the spinal cord (e.g., to increase excitability of neural networks present in the spinal cord), to stimulate or improve postural and/or locomotor activity and/or postural or locomotor strength, and/or reaching or grasping, and/or fine motor control of a hand in a human subject having a spinal cord injury, a brain injury, and/or a neurodegenerative pathology.

Numerous powered and non-powered orthotic exoskeletons are known to those of skill in the art. Suitable exoskeletons include, but are not limited to single joint orthoses (e.g., ankle foot orthoses, active knee orthoses, and full leg orthoses (e.g., EKSO GT™ (Ekso Bionics) as described herein. For a discussion of various orthotic exoskeleton systems, see Dollar and Herr (2008) *IEEE Trans. Robotics*, 24(1): 144-148).

Numerous powered orthotic exoskeletons are known to those of skill in the art, (see, e.g., U.S. Patent No: US 2016/0158593, US 2016/0206497, US 2016/0151176, US 2016/0128890, US 2016/0067137, US 2016/0045385, US 2016/0030201, US 2015/0338189, US 2015/0321341, US 2015/0290818, US 2015/0209214, US 2015/0134078, US 2015/0127118, US 2014/0213951, US 2014/0100493, US 2013/0289452, US 2013/0261513, US 2013/0253385, US 2013/0226048, US 2013/0158438, US 2013/0102935, US 2013/0040783, US 2010/0113987, US 2009/0292369, and the like) and can readily be adapted for use in the methods and systems described herein.

Figure 4:
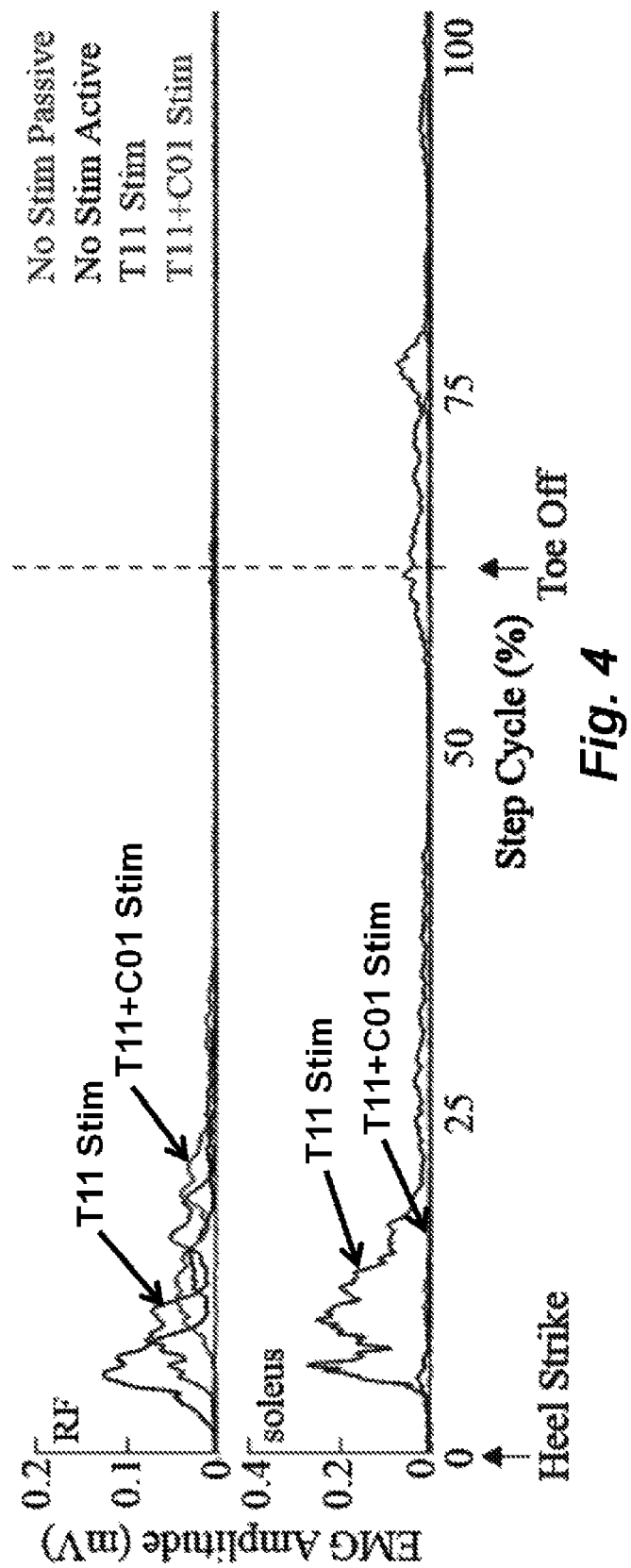
FIG. 4 shows mean EMG activity (30 consecutive steps) from the RF and soleus muscles during a normalized step cycle with and without stimulation at T11 and T11+Co1 during active (with voluntary effort) and a passive (without voluntary effort) mode.

By way of illustration, FIG. 1 from U.S. Patent Publication No: US 2016/0030201 A1 is shown in FIG. 4. This figure illustrates a side view of a person wearing an exoskeleton 100 (e.g., EKSO). As illustrated, and described in US 2016/0030201, the exoskeleton comprises a trunk portion a trunk portion 110 and lower leg supports 112 and can be used in combination with a walking aid 102 (depicted as a forearm crutch in the figure), including a lower, ground engaging tip 101 and a handle 103, by a person or wearer 109 to walk. As illustrated the wearer 109 is shown to have an upper arm 111, a lower arm (forearm) 122, a head 123 and lower limbs 124. In a manner known in the art, trunk portion 110 is configurable to be coupled to an upper body (not separately labeled) of the wearer 109, the leg supports 112 are configurable to be coupled to the lower limbs 124 of the person 109 and actuators, generically indicated at 125 but actually interposed between portions of the leg supports 112 as well as between the leg supports 112 and trunk portion 110 in a manner widely known in the art, for shifting of the leg supports 112 relative to the trunk portion 110 to enable movement of the lower limbs 124 of the wearer 109. In some embodiments, trunk portion 110 may be quite small and comprise a pelvic link wrapping around the pelvis of wearer 109. In the example shown in this figure, the exoskeleton actuators 125 are specifically shown as a hip actuator 135 which can be used to move hip joint 145 in flexion and extension, and a knee actuator 140 that can be used to move knee joint 150 in flexion and extension. The exoskeleton actuators 125 are controlled by CPU 120.

It will be recognized that this is but one illustrative lower limb exoskeleton that can be used in the methods and systems described herein. In certain embodiments the exoskeleton can comprise lower limb powered orthotic component(s) and/or upper limb powered orthotic components. In certain embodiments the exoskeleton can comprise lower limb non-powered orthotic component(s) and/or upper limb non-powered orthotic components. In other embodiments only a lower limb or only an upper limb orthotic exoskeletal component is utilized.

Figure 2:
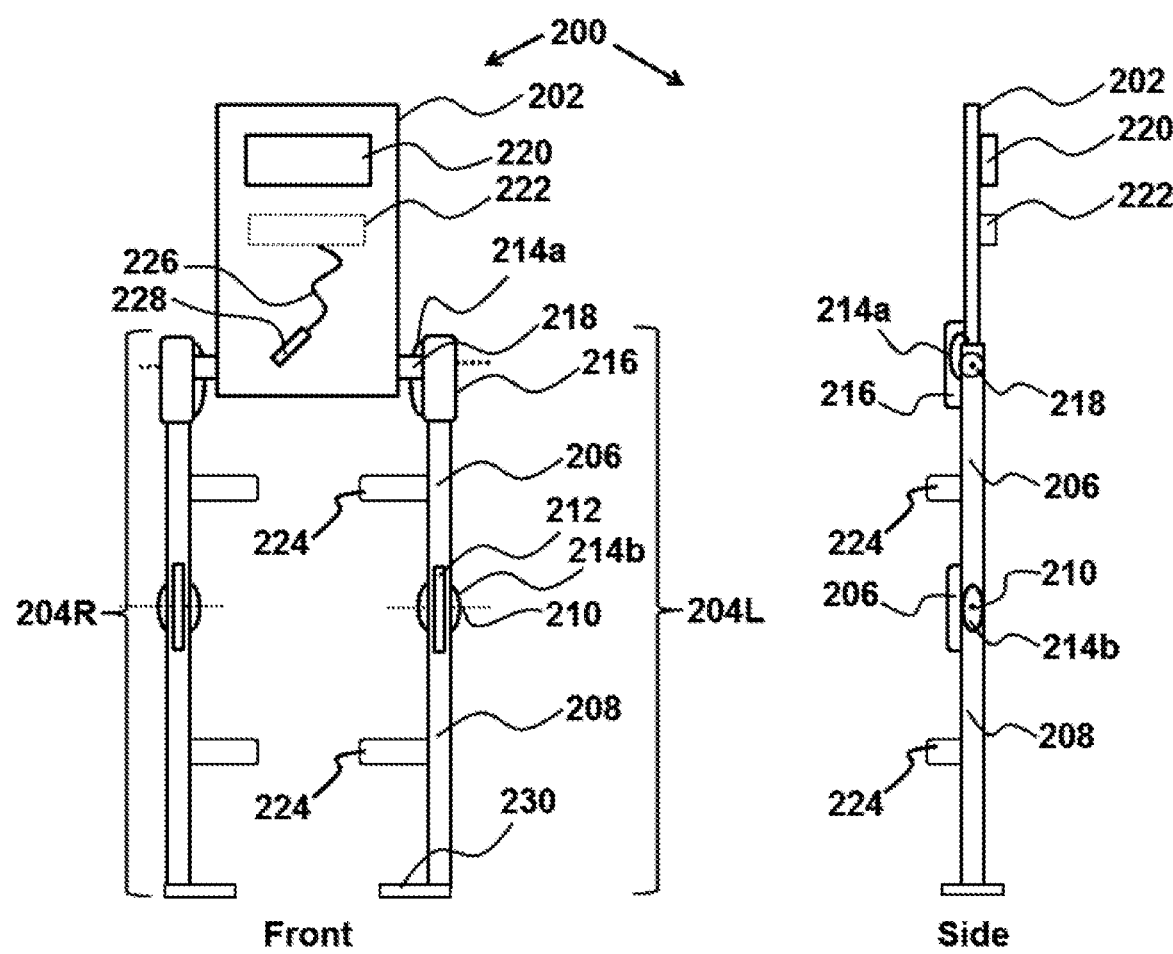
FIG. 2 schematically illustrates a powered exoskeleton system configured for control of the lower body limbs.
Figure 3:
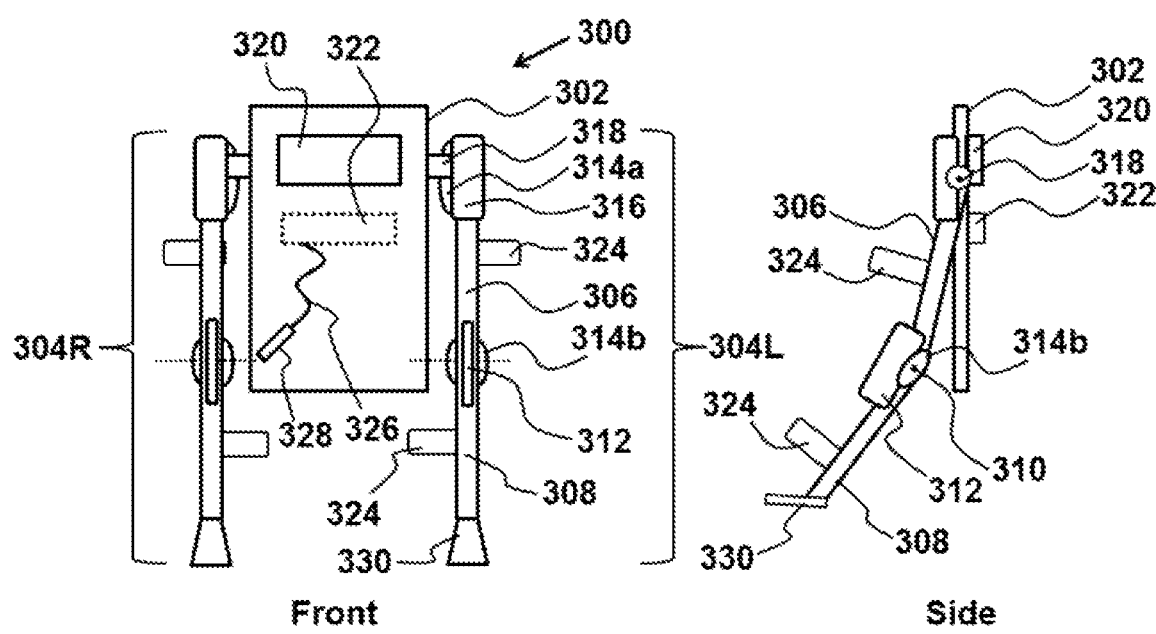
FIG. 3 schematically illustrates a powered exoskeleton system configured for control of the upper body limbs.

One illustrative, but non-limiting, embodiment of exoskeletal orthotic units that can be used in the systems and methods described herein is schematically illustrated in FIG. 2 (front view on the left and side view on the right). As illustrated the exoskeletal system comprises a powered orthotic system 200 comprising a torso portion 202 configured to be coupled to an upper body of a person and a lower limb orthotic component 204 (204R (right) and/or 204L (left) lower limb orthotic components) configured to provide assistance in locomotion of a lower limb and/or an upper limb powered orthotic component, e.g., as described below and illustrated in FIG. 3 configured to provide assistance in positioning and/or locomotion of an upper limb. In various embodiments the orthotic system comprises a plurality of sensors (e.g., 214a, 214b) for monitoring positions of the lower limb orthotic component. The exoskeletal orthotic system typically comprises a controller 220 configured to receive input from the sensors and to control assistance provided by the lower limb orthotic component and/or configured to control assistance provided by the upper limb orthotic component. While FIGS. 2 and 3 illustrate the controller integrated with the torso portion of the exoskeletal system, in certain embodiments the controller can be removable, and in other embodiments the controller can be generally provided as a separate unit. In certain embodiments the controller communicates with the exoskeleton elements through a wired connection, while in other embodiments the controller communicates with the exoskeleton wirelessly.

In various embodiments the lower limb orthotic component 204L and/or 204R comprises functions to provide at least one leg support (e.g., 206 in combination with 208) (configurable to be coupled e.g., via a strap 224) to a first lower limb of the person, with the at least one leg support including at least a thigh link 206 rotatably connectable to the torso portion 202 at a hip joint 218, and a shank link 208 rotatably connectable to the thigh link at a knee joint 210. Typically the lower limb orthotic component comprises a first lower limb actuator 216 for controlling motion of the hip joint; and a second lower limb actuator 212 for controlling motion of the knee joint. In certain embodiments to containing sensors that monitor positions of the lower limb orthotic components, in certain embodiments, the lower limb orthotic components contain sensors that measure force exerted by the user against the exoskeleton to facilitate calibration of the degree of augmentation provided. As illustrated in FIG. 2, in certain embodiments, the lower limb orthotic components can comprise a support 230 for the foot.

Another illustrative, but non-limiting, embodiment of an upper limb (upper body) exoskeletal orthotic unit that can be used in the systems and methods described herein is schematically illustrated in FIG. 3 (front view on the left and side view on the right). As illustrated in FIG. 3, the exoskeletal system comprises a powered orthotic system 300 comprising a torso portion 302 configured to be coupled to an upper body of a person and a lower limb orthotic component 304 (204R (right) and/or 204L (left) upper limb orthotic components) configured to provide assistance in the movement and/or stabilization of an upper limb. In various embodiments the orthotic system comprises a plurality of sensors (e.g., 314a, 314b) for monitoring positions of the lower limb orthotic component. The exoskeletal orthotic system typically comprises a controller 320 configured to receive input from the sensors and to control assistance provided by the upper limb orthotic component and/or configured to control assistance provided by the upper limb orthotic component.

In various embodiments the upper limb orthotic component 304L and/or 304R comprises functions to provide at least one arm support (e.g., 306 in combination with 308) (configurable to be coupled e.g., via a strap 324) to a first upper limb of the person, with the at least one upper limb support including at least a including at least an upper arm (brachium) link rotatably 306 rotatably connected to the torso portion 302 at a shoulder joint 318, and a forearm (antebrachium) link 308 rotatably connected to the thigh link at an elbow joint 310. Typically the upper limb orthotic component comprises a first upper limb actuator 316 for controlling motion of the shoulder joint; and a second upper limb actuator 312 for controlling motion of the elbow joint. As illustrated in FIG. 3, in certain embodiments, the lower limb orthotic components can comprise a support 330 for the hand.

In certain embodiments, in addition to containing sensors that monitor positions of the lower limb and/or upper limb orthotic components, the exoskeletons contain sensors that measure force exerted by the user against the exoskeleton to facilitate calibration of the degree of augmentation provided. As illustrated in FIG. 2, in certain embodiments, the lower limb orthotic components can comprise a support 230 for the foot.

Although not shown in certain embodiments, various sensors in communication with the controller (e.g., CPU) can be provided so that the controller can monitor the orientation of the device, and wearer. Such sensors may include, without restriction, encoders, potentiometers, accelerometers, and gyroscopes. In certain embodiments the exoskeleton (e.g., the EKSO GT™) can contain various tilt and position sensors that maintain the position of various joints within a fixed trajectory. It was discovered that tonic or intermittent transcutaneous electrical spinal cord stimulation can be used to re-engage the spinal circuitry to facilitate stepping in the EKSO and to progressively recover voluntary control of specific joint movements after complete paralysis.

In certain embodiments the controller is configured to control the various actuators with adaptive, variable levels of assistance in response to signals from the plurality of sensors. As the particular structure of the exoskeleton can take various forms, and such exoskeletons are known in the art further detail is not required herein.

As described herein in certain embodiments, systems are provided where a transcutaneous electrical stimulator (222 in FIG. 2, 322 in FIG. 3) is present to provide transcutaneous electrical stimulation to the user during operation of the exoskeleton. In certain embodiments the transcutaneous stimulator can be connected by one or more leads (226 in FIG. 2, 326 in FIG. 3) to provide a stimulation signal to an electrode (228 in FIG. 2, 328 in FIG. 3) which is applied to the skin surface of the subject, e.g., at one or more locations disposed over the spinal cord. In certain embodiments the transcutaneous stimulator is configured with the orthotic exoskeleton to create a closed loop system; whereby information from the exoskeleton system is received by the stimulator and interpreted by means of a machine learning algorithm to adjust the stimulation patterns.

The foregoing configurations of exoskeletons and stimulators are illustrative and non-limiting. Using the teachings provided herein numerous other configurations and systems will be available to one of skill in the art.

Transcutaneous Stimulation

Without being bound by a particular theory, it is believed that transcutaneous stimulation, e.g., over one spinal level, over two spinal levels, or over three spinal levels providing stimulation simultaneously, or in sequence, intermittently or continuously optionally in combination with use of the powered exoskeleton as described herein can facilitate recovery of stepping and standing (or other locomotor function) in human subjects following a partial or complete spinal cord injury, a brain injury, or a neurodegenerative pathology. Thus the methods described herein find use in subjects with a motor incomplete or motor complete spinal cord injury, in subjects with an ischemic brain injury (e.g., from stroke or acute trauma), and in subjects with a neurodegenerative pathology (e.g., stroke, Parkinson's disease, Huntington's disease, Alzheimer's disease, multiple sclerosis (MS), amyotrophic lateral sclerosis (ALS), primary lateral sclerosis (PLS), dystonia, cerebral palsy, and the like).

In some embodiments, the location of electrode(s) in addition to the stimulation parameters may be important in defining the motor response. The use of surface electrode(s), as described herein, facilitates selection or alteration of particular stimulation sites as well as the application of a wide variety of stimulation parameters.

In certain embodiments, the transcutaneous electrodes are disposed on the surface of a subject in one or more locations to stimulate the spinal cord (or regions thereof) and thereby activate various central pattern generators and restore endogenous activation patterns to stimulate or improve postural and/or locomotor activity and/or postural or locomotor strength, and/or reaching or grasping and/or hand or upper limb strength, and/or to enable one or more functions such as voluntary voiding of the bladder and/or bowel, sexual function, autonomic control of cardiovascular function, control/regulation of body temperature control, control of digestive functions, control of kidney functions, chewing, swallowing, drinking, talking, or breathing in a normal subject or a subject having a neurologically derived paralysis. The methods typically involve neuromodulating the spinal cord of the subject or a region thereof by administering transcutaneous stimulation to one or more locations on the spinal cord or a region thereof using an electrical stimulator electrically coupled to one or more transcutaneous electrodes and/or electrode arrays. In certain embodiments the transcutaneous electrodes described herein are disposed over the spinal cord or over one or more regions thereof.

Accordingly, in various embodiments methods and devices are provided to facilitate movement in a mammalian subject (e.g., a human) having spinal cord injury, brain injury, or neurological disease. In certain embodiments the methods involve transcutaneous stimulation of the spinal cord of the subject, in combination with use of the orthotic exoskeleton, where the stimulation modulates the electrophysiological properties of selected spinal circuits in the subject so they can be activated, e.g., by proprioceptive derived information and/or from supraspinal input.

In particular illustrative embodiments, the devices (systems) and methods described herein stimulate the spinal cord to modulate the proprioceptive and/or supraspinal information that controls the lower limbs during standing and/or stepping and/or the upper limbs during reaching and/or grasping conditions. This "sensory" and "motor" information can guide the activation of the muscles via spinal networks in a coordinated manner and in a manner that accommodates the external conditions, e.g., the amount of loading, speed and direction of stepping or whether the load is equally dispersed on the two lower limbs, indicating a standing event, alternating loading indicating stepping, or sensing postural adjustments signifying the intent to reach and grasp.

Unlike approaches that involve specific stimulation of motor neurons to directly induce a movement, the methods described herein enable the spinal circuitry to control the movements. More specifically, the devices and methods described herein exploit the spinal circuitry and its ability to interpret proprioceptive and/or cutaneous information and to respond to that proprioceptive and/or cutaneous information in a functional way. For example, the human spinal cord can receive sensory input associated with a movement such as stepping, and this sensory information can be used to modulate the motor output to accommodate the appropriate speed of stepping and level of load that is imposed on lower limbs. In some embodiments, the present methods can utilize the central-pattern-generation-like properties of the human spinal cord (e.g., the lumbosacral spinal cord, the thoracic spinal cord, the cervical spinal cord). Thus, for example, exploiting inter alia the central-pattern-generation-like properties of the lumbosacral spinal cord, oscillations of the lower limbs can be induced simply by vibrating the vastus lateralis muscle of the lower limb, and/or by transcutaneous stimulation of the spinal cord and/or ganglia, and/or by stretching the hip. The methods described herein exploit the fact that the human spinal cord, in complete or incomplete SCI subjects, can receive and interpret proprioceptive and somatosensory information that can be used to control the patterns of neuromuscular activity among the motor pools necessary to generate particular movements, e.g., standing, stepping, reaching, grasping, and the like. In various embodiments this is in contrast to other approaches where the actual movement is induced/controlled by direct stimulation (e.g., of particular motor neurons and/or muscles).

In one illustrative embodiment, the subject is fitted with one or more transcutaneous stimulation electrodes (or electrode arrays) described herein that afford selective stimulation and control capability to select sites, mode(s), and intensity of stimulation via electrodes placed over, for example, the lumbosacral spinal cord, and/or the thoracic spinal cord, and/or cervical spinal cord and/or brainstem to facilitate movement of the arms and/or legs of individuals with a spinal cord injury or another severely debilitating neuromotor disorder.

In certain embodiments the transcutaneous electrodes (or electrode arrays) herein can be disposed on the surface of the subject and typically the subject can be immediately tested to identify the most effective subject specific stimulation paradigms for facilitation of movement (e.g., stepping and standing and/or arm and/or hand movement). In certain embodiments, using these stimulation paradigms the subject can practice standing and stepping and/or reaching or grabbing in an interactive rehabilitation program while being subject to spinal stimulation. In certain embodiments this localization of stimulation is performed in conjunction with the use of the exoskeleton.

Depending on the site/type of injury and the locomotor and motor activity it is desired to facilitate particular spinal stimulation protocols include, but are not limited to specific stimulation sites along the lumbosacral and/or thoracic, and/or cervical spinal cord; specific combinations of stimulation sites along the lumbosacral and/or thoracic, and/or cervical spinal cord; specific stimulation amplitudes; specific stimulation polarities (e.g., monopolar and bipolar stimulation modalities); specific stimulation frequencies; and/or specific stimulation pulse widths.

In various embodiments, the methods described herein can comprise transcutaneous stimulation of one or more regions of the spinal cord and/or brain, and/or brain stem, and/or the coccygeal nerve (e.g., Co1) in combination with locomotor or motor activities provided/induced by the exoskeleton thereby providing modulation of the electrophysiological properties of spinal circuits in the subject so they are activated by proprioceptive information derived from the region of the subject where locomotor or motor activity is to be facilitated. Further, spinal stimulation in combination with pharmacological agents and locomotor or motor activity may result in the modulation of the electrophysiological properties of spinal circuits in the subject so they are activated by proprioceptive information derived from the region of the subject where locomotor or motor activity is to be facilitated.

In certain embodiments locomotor activity of the region of interest can be assisted or accompanied by any of a number of methods known. For example by way of illustration, individuals after severe SCI can generate standing and stepping patterns when provided with body weight support from the exoskeleton while on a treadmill. During both stand and step training of human subjects with SCI, the subjects in an exoskeleton can be placed on a treadmill in an upright position and, the exoskeleton can provide sufficient support to avoid knee buckling and trunk collapse. During bilateral standing, both legs can be loaded simultaneously with the degree of load being determined by the exoskeleton and extension can be the predominant muscular activation pattern, although co-activation of flexors can also occur. Additionally, or alternatively, during stepping the legs can be loaded in an alternating pattern by the exoskeleton and extensor and flexor activation patterns within each limb also alternated as the legs moved from stance through swing.

Transcutaneous Stimulation of a Region of the Thoracic Spine

In various embodiments, the methods described herein involve transcutaneous electrical stimulation of the thoracic spinal cord or a region of the thoracic spinal cord of the subject utilizing one or more of the transcutaneous electrodes and/or electrode arrays as described herein. Illustrative regions include, but are not limited to, one or more regions straddling or spanning a region selected from the group consisting of T1-T1, T1-T2, T1-T3, T1-T4, T1-T5, T1-T6, T1-T7, T1-T8, T1-T9, T1-T10, T1-T11, T1-T12, T2-T1, T2-T2, T2-T3, T2-T4, T2-T5, T2-T6, T2-T7, T2-T8, T2-T9, T2-T10, T2-T11, T2-T12, T3-T1, T3-T2, T3-T3, T3-T4, T3-T5, T3-T6, T3-T7, T3-T8, T3-T9, T3-T10, T3-T11, T3-T12, T4-T1, T4-T2, T4-T3, T4-T4, T4-T5, T4-T6, T4-T7, T4-T8, T4-T9, T4-T10, T4-T11, T4-T12, T5-T1, T5-T2, T5-T3, T5-T4, T5-T5, T5-T6, T5-T7, T5-T8, T5-T9, T5-T10, T5-T11, T5-T12, T6-T1, T6-T2, T6-T3, T6-T4, T6-T5, T6-T6, T6-T7, T6-T8, T6-T9, T6-T10, T6-T11, T6-T12, T7-T1, T7-T2, T7-T3, T7-T4, T7-T5, T7-T6, T7-T7, T7-T8, T7-T9, T7-T10, T7-T11, T7-T12, T8-T1, T8-T2, T8-T3, T8-T4, T8-T5, T8-T6, T8-T7, T8-T8, T8-T9, T8-T10, T8-T11, T8-T12, T9-T1, T9-T2, T9-T3, T9-T4, T9-T5, T9-T6, T9-T7, T9-T8, T9-T9, T9-T10, T9-T11, T9-T12, T10-T1, T10-T2, T10-T3, T10-T4, T10-T5, T10-T6, T10-T7, T10-T8, T10-T9, T10-T10, T10-T11, T10-T12, T11-T1, T11-T2, T11-T3, T11-T4, T11-T5, T11-T6, T11-T7, T11-T8, T11-T9, T11-T10, T11-T11, T11-T12, T12-T1, T12-T2, T12-T3, T12-T4, T12-T5, T12-T6, T12-T7, T12-T8, T12-T9, T12-T10, T12-T11, T12-T12, T12-L1, and L5 to S1. In certain embodiments the transcutaneous stimulation is to a region over T11.

Transcutaneous Stimulation of the Lumbosacral Spinal Cord.

In various embodiments, the methods described herein involve transcutaneous electrical stimulation of the lumbosacral spinal cord or a region of the lumbosacral spinal cord of the subject utilizing a transcutaneous electrodes and/or electrode arrays. Illustrative regions include, but are not limited to, one or more regions straddling or spanning a region selected from the group consisting of L1-L1, L1-L2, L1-L3, L1-L4, L1-L5, L2-L1, L2-L2, L2-L3, L2-L4, L2-L5, L3-L1, L3-L2, L3-L3, L3-L4, L3-L5, L4-L1, L4-L2, L4-L3, L4-L4, L4-L5, L5-L1, L5-L2, L5-L3, L5-L4, L5-L5, L5-S1. In certain embodiments transcutaneous stimulation is applied on the skin surface over a region comprising the coccygeal nerve Co1. In certain embodiments the transcutaneous stimulation is to both a region over T11 and to a region over Co1.

Transcutaneous Stimulation of a Region of the Cervical Spine

In certain embodiments, particular where upper limb activation is desired the methods described herein can involve transcutaneous electrical stimulation of the cervical spinal cord or a region of the cervical spinal cord of the subject utilizing one or more of the transcutaneous electrodes and/or electrode arrays. Illustrative regions include, but are not limited to, one or more regions straddling or spanning a region selected from the group consisting of C0-C1, C0-C2, C0-C3, C0-C4, C0-C5, C0-C6, C0-C7, C1-C1, C1-C2, C1-C3, C1-C4, C1-C7, C1-C6, C1-C7, C1-T1, C2-C2, C2-C3, C2-C4, C2-C5, C2-C6, C2-C7, C2-T1, C3-C3, C3-C4, C3-C5, C3-C6, C3-C7, C3-T1, C4-C4, C4-C5, C4-C6, C4-C7, C4-T1, C5-C5, C5-C6, C5-C7, C5-T1, C6-C6, C6-C7, C6-T1, C7-C7, and C7-T1.

Transcutaneous Stimulation Parameters.

In certain embodiments, the transcutaneous stimulation is at a frequency ranging from about 0.5 Hz, or 3 Hz, or from about 5 Hz, or from about 10 Hz, up to about 1,000 Hz, or up to about 500 Hz, or up to about 100 Hz, or up to about 80 Hz, or up to about 40 Hz, or from about 3 Hz or from about 5 Hz up to about 80 Hz, or from about 5 Hz up to about 30 Hz, or up to about 40 Hz, or up to about 50 Hz.

In certain embodiments, the transcutaneous stimulation is applied at an intensity (amplitude) ranging from about 10 mA up to about 500 mA, or up to about 300 mA, or up to about 150 mA, or from about 20 mA up to about 300 mA, or up to about 50 mA or up to about 100 mA, or from about 20 mA or from about 30 mA, or from about 40 mA up to about 50 mA, or up to about 60 mA, or up to about 70 mA or up to about 80 mA.

In certain embodiments, the pulse width ranges from about 100 µs up to about 200 ms, or from about 100 µs, or from about 150 µs, or from about 200 µs, up to about 900 µs, or up to about 800 µs, or up to about 700 µs, or up to about 600 µs, or up to about 500 µs, or up to about 450 µs, or from about 1 ms, or from about 2 ms, or from about 5 ms, or from about 10 ms, or from about 20 ms, or from about 50 ms up to about 200 ms, or up to about 150 ms, or up to about 100 ms, or up to about 80 ms, or up to about 60 ms.

In certain embodiments the stimulation pulse is delivered superimposed on a high frequency carrier signal. In certain embodiments the high frequency ranges from about 3 kHz, or about 5 kHz, or about 8 kHz up to about 100 kHz, or up to about 80 kHz, or up to about 50 kHz, or up to about 40 kHz, or up to about 30 kHz, or up to about 20 kHz, or up to about 15 kHz. In certain embodiments the carrier frequency amplitude ranges from about 30 mA, or about 40 mA, or about 50 mA, or about 60 mA, or about 70 mA, or about 80 mA up to about 500 mA, or up to about 400 mA, or up to about 300 mA, or up to about 200 mA, or up to about 150 mA.

In one illustrative, but non-limiting embodiment, a bipolar rectangular stimulus (1-msec duration) with a carrier frequency of 10 kHz and at intensities ranging from 30 to 300 mA is used. The stimulation can be at 5 Hz, for example, with an illustrative, but non-limiting exposure duration ranging from 10 to 30 sec. An illustrative, but non-limiting signal intensity is from about 80 mA, or from about 100 mA, or from about 110 mA to about 200 mA, or about 180 mA, or to about 150 mA.

In certain embodiments the transcutaneous stimulation is at a frequency and amplitude sufficient to stimulate or improve postural and/or locomotor activity and/or postural or locomotor strength. In certain embodiments the transcutaneous stimulation is at a frequency and amplitude sufficient to stimulate or improve postural and/or locomotor activity and/or postural or locomotor strength when applied in conjunction with a neuromodulatory agent (e.g., a monoaminergic agent). In certain embodiments the transcutaneous stimulation is at a frequency and amplitude sufficient to stimulate grasping, and/or improve hand strength and/or fine hand control. In certain embodiments the transcutaneous stimulation is at a frequency and amplitude sufficient to improve stimulate grasping and/or to improve hand strength and/or fine hand control when applied in conjunction with a neuromodulatory agent (e.g., a monoaminergic agent). In certain embodiments the transcutaneous stimulation is at a frequency and amplitude sufficient to stimulate voluntary voiding of the bladder and/or bowel, and/or return of sexual function, and/or autonomic control of cardiovascular function, and/or body temperature, control of digestive functions, control of kidney functions, chewing, swallowing, drinking, talking, or breathing in a normal subject or a subject having a neurologically derived paralysis. In certain embodiments the transcutaneous stimulation is at a frequency and amplitude sufficient to stimulate voluntary voiding of the bladder and/or bowel, and/or return of sexual function, and/or autonomic control of cardiovascular function, and/or body temperature when applied in conjunction with a neuromodulatory agent (e.g., a monoaminergic agent). In certain embodiments the carrier frequency, when present, is at frequency and intensity sufficient to minimize subject discomfort.

By way of illustration, non-invasive transcutaneous electrical spinal cord stimulation (tSCS) can induce locomotor or motor-like activity in non-injured humans. Continuous tSCS (e.g., at 5-40 Hz) applied paraspinally over the T11-T12 vertebrae can induce involuntary stepping movements in subjects with their legs in a gravity-independent position. These stepping movements can be enhanced when the spinal cord is stimulated at two to three spinal levels (C5, T12, and/or L2) simultaneously with frequency in the range of 5-40 Hz. Further, locomotion can be improved, in some embodiments substantially, when locomotor and postural spinal neuronal circuitries are stimulated simultaneously.

In another illustrative, but non-limiting embodiment transcutaneous electrical stimulation (5 Hz) delivered simultaneously at the T11, and Co1 vertebral levels facilitated involuntary stepping movements that were significantly stronger than stimulation at T11 alone. Accordingly, simultaneous spinal cord stimulation at multiple sites can have an interactive effect on the spinal circuitry responsible for generating locomotion.

International Patent Publication No: WO/2012/094346 demonstrates that locomotor activity and/or strength and/or posture can be improved and/or restored by stimulation of the spinal circuitry. The methods described in WO/2012/094346 can be further enhanced by the use of the robotic exoskeletons as described herein.

With respect to hand control, it is noted that WO/2015/048563 (PCT/US2014/057886) shows that the cervical spinal cord can be neuromodulated using two paradigms, i.e., electrically and pharmacologically. Moreover, the data presented therein indicate that non-functional networks can become engaged and progressively improve motor performance. In addition, the further improvement in hand function after withdrawing painless cutaneous enabling motor control (pcEmc) and pharmacological Enabling motor control *(fEmc) suggests that once functional connections are established they remain active. The methods described in WO/2015/048563 can be further enhanced by the use of robotic exoskeletons as described herein.

Application of Transcutaneous Electrode Arrays.

As noted above, the transcutaneous electrodes or electrode arrays may applied to the surface of a body using any of a number of methods well known to those of skill in the art.

In one embodiment, the subject is fitted with one or more transcutaneous electrodes and/or electrode arrays described herein that afford selective stimulation and control capability to select sites, mode(s), and intensity of stimulation via electrodes placed superficially over, for example, the lumbosacral spinal cord and/or the thoracic spinal cord, and/or the cervical spinal cord to facilitate movement of the arms and/or legs of individuals with a severely debilitating neuromotor disorder.

In some embodiments, the subject is provided a generator control unit and is fitted with an electrode(s) and then tested to identify the most effective subject specific stimulation paradigms for facilitation of movement (e.g., stepping and standing and/or arm and/or hand movement). Using the herein described stimulation paradigms, the subject practices standing, stepping, sitting, postural control, reaching, grabbing, pushing, pulling, breathing, and/or speech therapy in an interactive rehabilitation program while being subject to spinal stimulation.

Depending on the site/type of injury and the locomotor or motor activity it is desired to facilitate, particular spinal stimulation protocols include, but are not limited to, specific stimulation sites along the lumbosacral, thoracic, cervical spinal cord or a combination thereof; specific combinations of stimulation sites along the lumbosacral, thoracic, cervical spinal cord and/or a combination thereof; specific stimulation amplitudes; specific stimulation polarities (e.g., monopolar and bipolar stimulation modalities); specific stimulation frequencies; and/or specific stimulation pulse widths; and/or specific waves forms (square wave, sine wave) and patterns (monophasic, bi-phasic), etc.

In various embodiments, the system is designed so that the patient can use and control it in the home environment.

In various embodiments, transcutaneous electrodes and/or electrode arrays are operably linked to control circuitry that permits selection of electrode(s) to activate/stimulate and/or that controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using, e.g., constant current or constant voltage delivery of the stimulation.

It will be recognized that any present or future developed stimulation system capable of providing an electrical signal to one or more regions of the spinal cord may be used in accordance with the teachings provided herein.

In one illustrative but non-limiting system a control module is operably coupled to a signal generation module and instructs the signal generation module regarding the signal to be generated. For example, at any given time or period of time, the control module may instruct the signal generation module to generate an electrical signal having a specified pulse width, frequency, intensity (current or voltage), etc. The control module may be preprogrammed prior to use or receive instructions from a programmer (or another source). Thus, in certain embodiments the pulse generator/controller is configurable by software and the control parameters may be programmed/entered locally, or downloaded as appropriate/necessary from a remote site.

In certain embodiments the control module is operably coupled to the orthotic exoskeleton system creating a closed loop system gathering and using information from the exoskeleton system to adjust the stimulation; by sending instructions to the signal generator.

In certain embodiments the pulse generator/controller may include or be operably coupled to memory to store instructions for controlling the stimulation signal(s) and may contain a processor for controlling which instructions to send for signal generation and the timing of the instructions to be sent.

While in certain embodiments, two leads are utilized to provide transcutaneous stimulation, it will be understood that any number of one or more leads may be employed. In addition, it will be understood that any number of one or more electrodes per lead may be employed. Stimulation pulses are applied to transcutaneous electrodes and/or electrode arrays (which typically are cathodes) with respect to a return electrode (which typically is an anode) to induce a desired area of excitation of electrically excitable tissue in one or more regions of the spine. A return electrode such as a ground or other reference electrode can be located on the same lead as a stimulation electrode. However, it will be understood that a return electrode may be located at nearly any location, whether in proximity to the stimulation electrode or at a more remote part of the body, or as part of a metallic case such as at a metallic case of a pulse generator. It will be further understood that any number of one or more return electrodes may be employed. For example, there can be a respective return electrode for each cathode such that a distinct cathode/anode pair is formed for each cathode.

In various embodiments, the approach is not to electrically induce a walking pattern, standing pattern, or moving pattern of activation, but to enable/facilitate it so that when the subject manipulates their body position, the spinal cord can receive proprioceptive information from the legs (or arms) that can be readily recognized by the spinal circuitry. Then, the spinal cord knows whether to step or to stand or to reach or to grasp, or to do nothing. In other words, this enables the subject to begin stepping or to stand or to reach and grasp when they choose after the stimulation pattern has been initiated.

Moreover, the methods and devices described herein are effective in a spinal cord injured subject that is clinically classified as motor complete; that is, there is no motor function below the lesion. In various embodiments, the specific combination of electrode(s) activated/stimulated and/or the desired stimulation of any one or more electrodes and/or the stimulation amplitude (strength) can be varied in real time, e.g., by the subject. Closed loop control can be embedded in the process by engaging the spinal circuitry as a source of feedback and feedforward processing of proprioceptive input and by voluntarily imposing fine tuning modulation in stimulation parameters based on visual, and/or kinetic, and/or kinematic input from selected body segments.

In various embodiments, the devices, optional pharmacological agents, and methods are designed so that a subject with no voluntary movement capacity can execute effective standing and/or stepping and/or reaching and/or grasping. In addition, the approach described herein can play an important role in facilitating recovery of individuals with severe although not complete injuries.

Use of Neuromodulatory Agents.

In certain embodiments, the stimulation methods described herein (e.g., noninvasive (e.g., transcutaneous) stimulation in combination with a robotic exoskeleton are used in conjunction with various pharmacological agents, particularly pharmacological agents that have neuromodulatory activity (e.g., that are monoamergic). In certain embodiments, the use of various serotonergic, and/or dopaminergic, and/or noradrenergic, and/or GABAergic, and/or glycinergic drugs is contemplated. These agents can be used in conjunction with transcutaneous stimulation and robotic aid as described above. This combined approach can help to put the spinal cord in an optimal physiological state for controlling a range of hand and/or upper limb movements or lower limb movements or for regulating posture, and the like.

In certain embodiments, the drugs are administered systemically, while in other embodiments, the drugs are administered locally, e.g., to particular regions of the spinal cord. Drugs that modulate the excitability of the spinal neuromotor networks include, but are not limited to combinations of noradrenergic, serotonergic, GABAergic, and glycinergic receptor agonists and antagonists.

Dosages of at least one drug or agent can be between about 0.001 mg/kg and about 10 mg/kg, between about 0.01 mg/kg and about 10 mg/kg, between about 0.01 mg/kg and about 1 mg/kg, between about 0.1 mg/kg and about 10 mg/kg, between about 5 mg/kg and about 10 mg/kg, between about 0.01 mg/kg and about 5 mg/kg, between about 0.001 mg/kg and about 5 mg/kg, or between about 0.05 mg/kg and about 10 mg/kg. Typically where the drug is an approved drug, it will be administered at dosage consistent with the recommended/approved dosage for that drug.

Drugs or agents can be delivery by injection (e.g., subcutaneously, intravenously, intramuscularly, intrathecal), orally, rectally, or inhaled.

Illustrative pharmacological agents include, but are not limited to, agonists and antagonists to one or more combinations of serotonergic: 5-HT1A, 5-HT2A, 5-HT3, and 5HT7 receptors; to noradrenergic alpha 1 and 2 receptors; and to dopaminergic D1 and D2 receptors (see, e.g., Table 1).

TABLE 1

Illustrative, but non-limiting pharmacological agents.

| Name | Target | Action | Route | Typical Dose (mg/Kg) | Typical Range (mg/kg) |
|---|---|---|---|---|---|
| Serotonergic receptor systems | | | | | |
| 8-OHDPAT | 5-HT1A7 | Agonist | S.C. | 0.05 | 0.045-0.3 |
| Way 100.635 | 5-HT1A | Antagonist | I.P. | 0.5 | 0.4-1.5 |
| Quipazine | 5-HT2A/C | Agonist | I.P. | 0.2 | 0.18-0.6 |
| Ketanserin | 5-HT2A/C | Antagonist | I.P. | 3 | 1.5-6.0 |
| SR 57227A | 5-HT3 | Agonist | I.P. | 1.5 | 1.3-1.7 |
| Ondanesetron | 5-HT3 | Antagonist | I.P. | 3 | 1.4-7.0 |
| SB269970 | 5-HT7 | Antagonist | I.P. | 7 | 2.0-10.0 |
| Buspirone | | | | | |
| Noradrenergic receptor systems | | | | | |
| Methoxamine | Alpha1 | Agonist | I.P. | 2.5 | 1.5-4.5 |
| Prazosin | Alpha1 | Antagonist | I.P. | 3 | 1.8-3.0 |
| Clonidine | Alpha2 | Agonist | I.P. | 0.5 | 0.2-1.5 |
| Yohimbine | Alpha2 | Antagonist | I.P. | 0.4 | 0.3-0.6 |
| Dopaminergic receptor systems | | | | | |
| SKF-81297 | D1-like | Agonist | I.P. | 0.2 | 0.15-0.6 |
| SCH-23390 | D1-like | Antagonist | I.P. | 0.15 | 0.1-0.75 |
| Quinipirole | D2-like | Agonist | I.P. | 0.3 | 0.15-0.3 |
| Eticlopride | D2-like | Antagonist | I.P. | 1.8 | 0.9-1.8 |

In certain embodiments the neuromodulatory agent (drug) is a molecule that activates (e.g., selectively activates) an α2c adrenergic receptor subtype and/or that blocks (e.g., selectively blocks) blocking an α2a adrenergic receptor subtype. In certain embodiments the molecule that activates an α2c adrenergic receptor subtype is 2-[(4,5-Dihydro-1H-imidazol-2-yl)methyl]-2,3-dihydro-1-methyl-1H-isoindole (BRL-44408). In certain embodiments the molecule that activates an α2c adrenergic receptor subtype is (R)-3-nitro-biphenyline and/or a compound according to the formula:

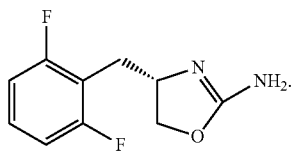 [SMILES: NC1=N[C@@H](Cc2c(F)cccc2F)CO1]

In certain embodiments the neuromodulatory agent comprises Clonidine. In certain embodiments the neuromodulatory agent further comprises a 5-HT1 and/or a 5-HT7 serotonergic agonist.

In certain embodiments the neuromodulatory includes any neuromodulatory agent or combination of agents described in US 2016/0158204 A1 which is incorporated herein by reference for the neuromodulatory agents and combinations thereof described therein.

EXAMPLES

The following examples are offered to illustrate, but not to limit the claimed invention.

Example 1

Iron 'ElectriRx' Man: Overground Stepping in an Exoskeleton Combined with Noninvasive Spinal Cord Stimulation after Paralysis Introduction Results in mice (Cai et al. (2006) *Philos. Trans. R. Soc. Lond. B. Biol. Sci.* 361: 1635-1646; Fong et al. (2005) *J. Neurosci.* 25: 11738-11747), rats (Courtine et al. (2009) *Nat. Neurosci.* 12: 1333-1342; van den Brand et al. (2012) *Science,* 336: 1182-1185), cats (Musienko et al. (2012) *J. Neurophysiol.* 107: 2072-2082; Musienko et al. (2012) *J. Neurosci.* 32: 17442-17453), and humans (Angeli et al. (2014) *Brain,* 137: 1394-1409; Harkema et al. (2011) *Lancet,* 377: 1938-1947) with motor complete paralysis have shown that the lumbosacral spinal circuitry can be neuromodulated using a combination of electrical epidural stimulation (Ichiyama et al. (2008) *J. Neurosci.* 28: 7370-7475; Lavrov et al. (2008) *J. Neurosci.* 28: 7774-7780), pharmacological interventions (Musienko et al. (2011) *J. Neurosci.* 31: 9264-9278), and locomotor training (Ichiyama et al. (2008) *J. Neurosci.* 28: 7370-7475; Barbeau and Rossignol (1994) *Curr. Opin. Neurol.* 7: 517-524) to enable weight-bearing standing (Harkema et al. (2011) *Lancet,* 377: 1938-1947; Gad et al. (2013) *J. Neuroeng. Rehabil.* 10: 2), stepping (Rossignol et al. (2006) *Physiol. Rev.* 86: 89-154; Edgerton et al. (2001)*J. Physiol.* 533: 15-22), voluntary movements (Angeli et al. (2014) *Brain,* 137: 1394-1409; Harkema et al. (2011) *Lancet,* 377: 1938-1947) and bladder control (Gad et al. (2014) *PLoS One,* 9: e 108184). We recently demonstrated the ability to noninvasively neuromodulate the lumbosacral neural circuitry to induce locomotor-like movements in healthy subjects using electromagnetic stimulation (Gerasimenko et al. (2010) *J. Neurosci.* 30: 3700-3708). Similar responses were observed using transcutaneous electrical spinal cord stimulation having a unique waveform that minimizes pain and discomfort in both healthy (Gorodnichev et al. (2012) *Fiziol. Cheloveka,* 38: 46-56) and paralyzed subjects.

Over the past several years, robotic therapy has been tested as a method to improve locomotion in paralyzed subjects with varying results. An assist-as-needed (AAN) paradigm was tested in mice using a specially designed robotic treadmill with arms to move the legs in a trajectory with an allowable error window (Fong et al. (2005) *J. Neurosci.* 25: 11738-11747). EKSO Bionics is a battery powered wearable bionic suit that enables individuals with lower extremity weakness to stand and step overground with partial weight bearing and reciprocal gait. The EKSO GT robotic exoskeleton used in this study is a class I medical device (United States FDA) that has the potential to facilitate functional rehabilitation. The variable assist mode offered by the EKSO allows active involvement of subjects having minimal voluntary ability and minimal supraspinal control (Angeli et al. (2014) *Brain,* 137: 1394-1409; Harkema et al. (2011) *Lancet,* 377: 1938-1947), even in patients with motor complete paralysis. Based on the effort applied by the subject, the onboard computer will provide the necessary assistance to complete the step cycle. The EKSO has several tilt and position sensors that maintain the position of various joints within a fixed trajectory. We hypothesized that tonic transcutaneous electrical spinal cord stimulation can be used to re-engage the spinal circuitry to facilitate stepping in the EKSO and to progressively recover voluntary control of specific joint movements after complete paralysis.

Methods

A. Clinical Assessment and Patient Information

The UCLA Review Board approved all procedures. The subject was a 38-year-old man at the time of the experiment. He lost his eyesight at the age of 22, and 4 years prior to the experiment fell from a second floor onto a concrete floor damaging his spinal cord at the T9 and L1 vertebral levels. He was assessed clinically as motor and sensory complete (AIS A). The subject had owned the EKSO bionics suit for ~2 years and had completed ~180,000 steps prior to the experiment. He signed an informed consent form. All experimental procedures were approved by the Institutional Review Board of the University of California, Los Angeles.

B. Training and Testing Procedures

The subject stepped in the EKSO for 1 hr/day in the active (with voluntary effort) mode with a 5 min warm-up in the passive (without voluntary effort) mode. The 1 hr session was divided into three 20-min laps (40 m in length). During the first lap, the stimulation was delivered at the T11 vertebral segment (30 Hz), the second involved stimulation at the Co1 vertebral level (5 Hz), and the third lap consisted of simultaneous stimulation at T11 and Co1. Blood pressure and heart rate were recorded at the end of each lap. At the end of 5 days of training, stepping ability was assessed while the subject walked in the EKSO with and without stimulation at T11 and/or Co1 in both a passive and an active mode. The following day, voluntary ability to perform movements in specific joints was assessed with and without stimulation at T11 and/or Co1 with the subject being in a supine position.

C. EMG and Kinematic Recordings

During every session, bipolar EMG surface electrodes were used to record bilaterally on the soleus, medial gastrocnemius (MG), tibialis anterior (TA), rectus femoris (RF) and vastus lateralis (VL) (Gorodnichev et al. (2012) *Fiziol. Cheloveka,* 38: 46-56). EMG signals were amplified differentially (bandwidth of 10 Hz to 5 KHz) and acquired at 10 KHz using a 16 channel hard-wired A/D board and a customized LabVIEW software (National Instruments, TX) acquisition program.

Results

Based on the subject's feedback, stimulation at T11 resulted in a feeling of 'tension' in all proximal lower limb muscles. The 'tension' was felt during sitting and increased when stepping (passive mode) in the EKSO. The tension greatly increased when the subject started stepping in the active mode. Tension was not felt with stimulation at Co1 when sitting and was minimal during passive stepping. During active stepping, however, the subject reported high levels of a tingling sensation in his entire leg, especially in the distal muscles, ankle joint and sole of the foot. During stimulation at T11+Co1, the subject reported tension and tingling in the entire leg. At the end of each 1-hr training session, perspiration was observed in different parts of the upper and lower back, the gluteus muscles, and the calf muscles. This was the first time the subject reported perspiration below the level of lesion since his spinal injury. During the 1-hr training session, the average heart rate increased from 75 to 110 beats/sec and the systolic and diastolic pressure changed from 95 to 72 and 140 to 89 mm of Hg, respectively.

Figure 5:
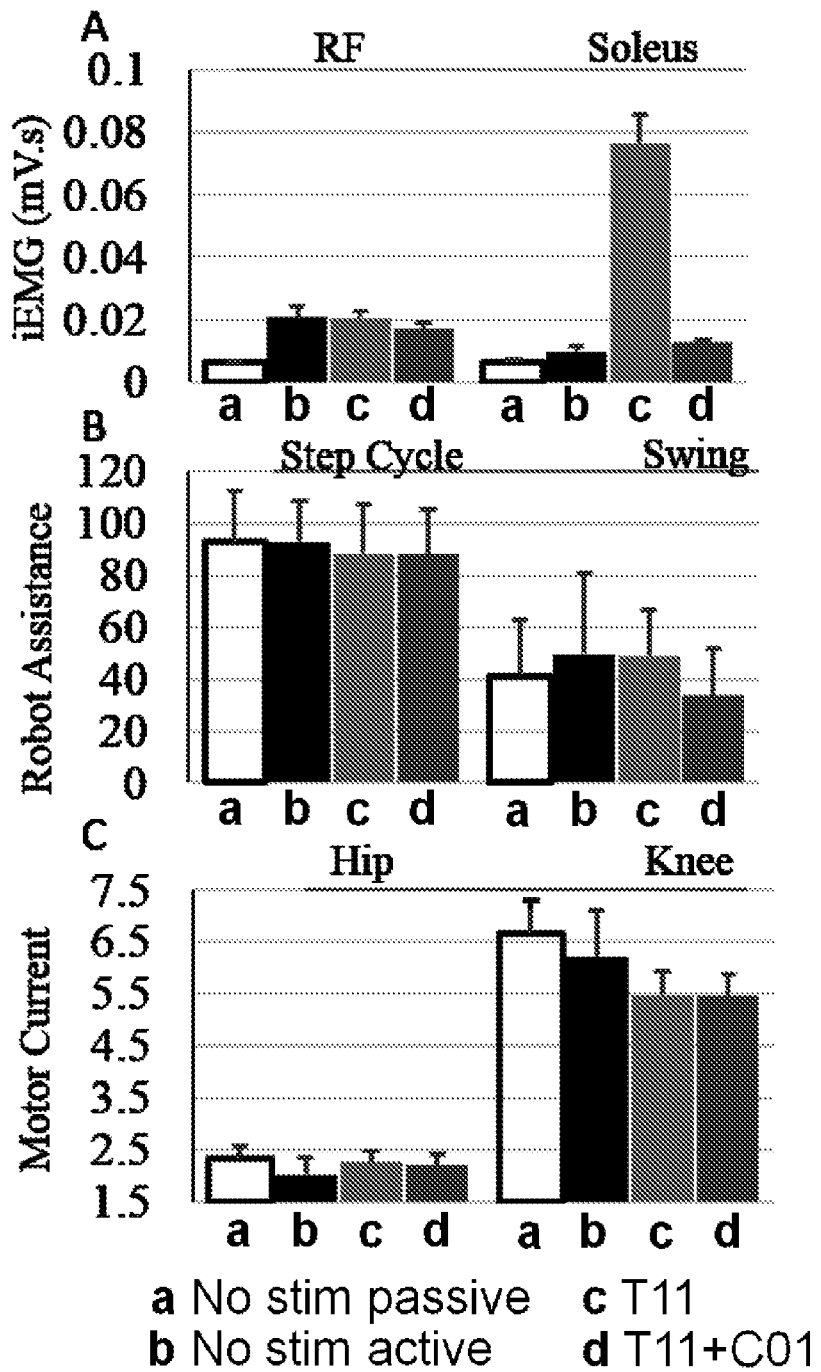
FIG. 5, panel A: Mean+SD (30 steps) iEMG from the RF and soleus muscles while stepping in the EKSO.
Figure 6:
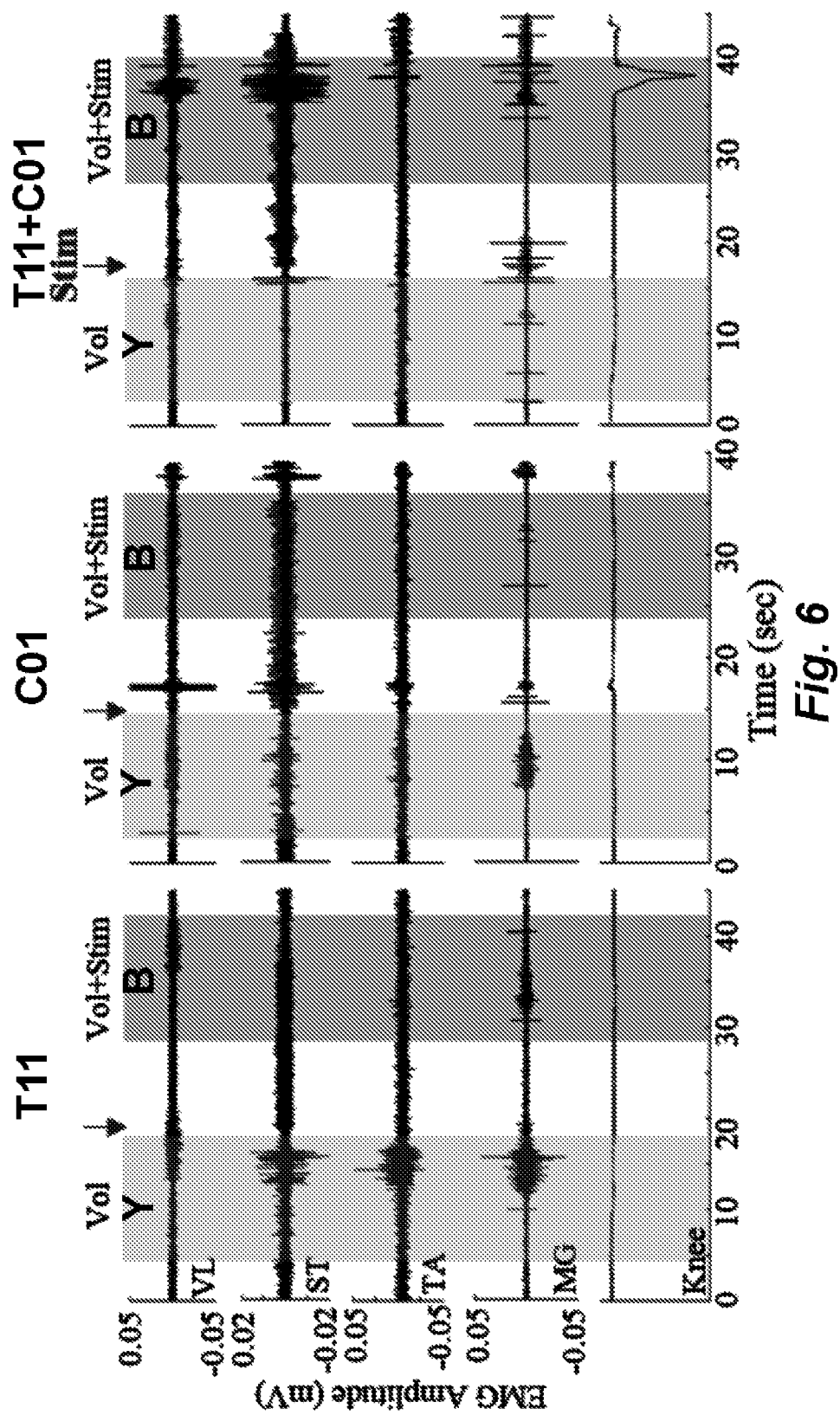
FIG. 6. Bandpass filtered EMG with the subject in supine position while attempting to flex the left knee with and without stimulation at T11 and/or Co1.

The EMG activity was higher during active compared to passive stepping without stimulation, especially in the RF (FIG. 4). With T11 stimulation the EMG activity was increased in the soleus muscles compared to No Stim with the activation being delayed in RF and lasting longer (FIG. 4). The assistance provided by the robot to maintain the path during the swing phase was greater during active compared to passive stepping without stimulation (FIG. 5, panel B) even though the current drawn by the knee and hip motors were reduced, probably due to reduced movement precision without stimulation. The robot assistance and motor current were lower during stimulation at T11 and T11+Co1 compared to no stimulation. These lower values with stimulation could be attributed to the increased sense of feeling in the legs during active stepping. The EMG activation pattern in the RF during T11+Co1 was further delayed compared to T11 alone with the burst lasting longer. To further examine changes in the neural networks, we tested the subject's ability to voluntarily move specific joints with and without stimulation at T11 and/or Co1 (FIG. 6). When the subject attempted to flex his knee with no stimulation (FIG. 6 shaded areas labeled "Y"), there was co-activation of the MG and soleus with the TA muscle. Little activation was observed in the proximal muscles. The EMG activity in all muscles was lower with stimulation at T11 or Co1 when the subject attempted to flex (FIG. 6, shaded areas labeled "B"). Although EMG activity was observed in all muscles, no change in knee angle was observed either with or without stimulation at T11 or Co1. During stimulation at T11+Co1, however, the subject was successful in flexing his knee completely and there were higher levels of EMG activity in all proximal muscles compared to stimulation at either site alone.

Discussion

Noninvasive Activation of the Spinal Cord

We have developed a novel method for noninvasively neuromodulating the spinal cord using painless transcutaneous stimulation using a special form of electrical pulses at a high frequency (Gerasimenko et al. (2010) *J. Neurosci.* 30: 3700-3708). This method enabled the activation of all leg muscles in a coordinated manner to aid in the performance of stepping in the EKSO as well as when performing voluntary tasks. This method has been shown to be effective in inducing locomotor-like activity in non-injured (Gorodnichev et al. (2012) *Fiziol. Cheloveka,* 38: 46-56) and SCI (under review) subjects when their legs were placed in a gravity-neutral position. As the subject is in a vertical position, combination partial weight bearing and activation of spinal neural networks via stimulation greatly enhances locomotor as well as autonomic functions.

Incongruity of Clinical and Physiological Assessments of Completeness of Paralysis We have reported changes in the physiological state of the spinal cord in 4 out of 4 clinically motor complete subjects implanted with a 16-electrode epidural array over the L1-S1 spinal levels within weeks of implantation (Angeli et al. (2014) *Brain,* 137: 1394-1409; Harkema et al. (2011) *Lancet,* 377: 1938-1947). The results show recovery and progressive improvement in volitional motor control as a result of daily motor training, but only in the presence of epidural stimulation. This increase in excitability was sufficiently close to the motor threshold so that the newly evolved supraspinal descending input to the lumbosacral spinal cord was sufficient to reach motor threshold. Kakulas (1999) *J. Spinal CordMed.* 22: 119-124, reported a remarkable finding in the study of 564 human cadavers with SCI. He studied variables such as axonal lesions, traumatic demyelination-remyelination, and quantification of white matter tracts. Surprisingly, many of the cadavers had a proportion of their spinal cord white matter remaining across the level of lesion even though they were completely paralyzed as assessed clinically. The changes in both locomotor and autonomic systems reported by the subject under the influence of stimulation and descending cortical control suggests that the spinal cord of a paralyzed subject clinically diagnosed at AIS A can be physiologically neuromodulated to a functional state Conclusion We have shown we can successfully neuromodulate the spinal cord neural circuitry controlling overground stepping in the EKSO via transcutaneous spinal cord stimulation and minimal descending control after complete paralysis. This change in excitability also enables voluntary control of legs, cardiovascular function, and thermoregulation.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for assisting a human subject with one or more functions, the human subject having at least one of: a spinal cord injury, a brain injury, and a neurodegenerative pathology, and the one or more functions comprising at least one of: postural stabilization, postural strength, locomotor activity, locomotor strength, reaching activity, and reaching strength, said method comprising:

applying transcutaneous stimulation to at least one of: a spinal cord, a brainstem, a brain, and sacral nerves of said subject, thereby activating neural networks of the spinal cord;

utilizing an exoskeletal system to expose said subject to proprioceptive signals associated with at least one of: postural changes, weight bearing, locomotor activity, and reaching; and whereby utilizing a combination of the transcutaneous stimulation and the exoskeletal system assists said subject in said one or more functions.

2. The method of claim 1, wherein the combination of said transcutaneous stimulation and said exoskeletal system modulates in real time spinal circuits in said subject so said spinal circuits are activated by proprioceptive signals produced in said subject by utilization of said exoskeletal system.

3. The method of claim 1, wherein the assistance provided by the combination of said transcutaneous stimulation and said exoskeletal system is synergistic.

4. The method of claim 1, wherein said exoskeletal system is configured for at least one of:
   partially or fully controlling movement of a leg, an arm, and/or a hand of said subject; and/or
   partially or fully controlling a load bearing positional change in a region of the subject where locomotor activity is to be facilitated;
   providing variable assistance where corrective assistance is provided based on an extent of deviation by the subject from a healthy or predetermined motion, or by a variation in resistance to a load provided by the subject;
   providing assistance to said subject in a standing position;
   providing assistance to said subject in rising to a standing position from a seated or reclining position;
   providing assistance to said subject in stepping;
   providing assistance to said subject in sitting down or laying down;
   providing assistance to said subject in stabilizing a sitting or a standing posture;
   providing assistance to said subject in reaching; and
   providing assistance to said subject in grasping.

5. The method of claim 1, wherein said transcutaneous stimulation comprises one or more of:
   a frequency comprising a range from about 0.5 Hz up to about 1,000 Hz,
   an amplitude comprising a range from 10 mA up to about 500 mA, and
   a pulse width comprising a range from about 100 µs up to about 200 ms.

6. The method of claim 1, wherein said transcutaneous stimulation is superimposed on a high frequency carrier signal.

7. The method of claim 6, wherein said high frequency carrier signal comprises one or more of:
   a frequency comprising a range from about 3 kHz up to about 100 kHz, and
   or
   an amplitude comprising a range from about 30 mA up to about 500 mA.

8. The method of claim 1, wherein said transcutaneous stimulation comprises one or more of:
   a monopolar configuration,
   a bipolar configuration,
   a monophasic configuration,
   a biphasic configuration,
   a tonic stimulation,
   stimulation of a single region of the spinal cord, and
   simultaneous or sequential stimulation of different spinal cord regions.

9. The method of claim 1, wherein said transcutaneous stimulation is applied on one or more skin surfaces associated with one or more of:
   a cervical spine a region, a thoracic spine region, a lumbosacral spine region,
   a region associated with the spinal cord that controls the lower limbs to stimulate locomotor activity or strength or to improve postural control,
   a thoracic spinal cord region, a lumbar spinal cord region,
   a region comprising T11,
   a region comprising the coccygeal nerve Co1,
   a region of the spinal cord that controls the upper limbs to improve reaching activity and/or reaching strength, and
   a region comprising the cervical spinal cord.

10. The method of claim 1, wherein the transcutaneous stimulation is under control of the subject, and/or said exoskeletal system is under control of the subject.

11. The method of claim 1, wherein said exoskeletal system comprises a wearable powered orthotic system.

12. The method of claim 11, wherein
   said wearable powered orthotic system comprises:
      a torso portion configured to be coupled to an upper body of said subject;
      a lower limb powered orthotic component configured to provide assistance in locomotion of a lower limb;
      an upper limb powered orthotic component configured to provide assistance in locomotion of an upper limb;
      a plurality of sensors for monitoring positions of said lower limb powered orthotic component and/or said upper limb powered orthotic component; and
      a controller configured to control assistance provided by said lower limb powered orthotic component and/or configured to control assistance provided by said upper limb powered orthotic component.

13. The method of claim 11, wherein said exoskeletal system comprises:
   a torso portion configurable to be coupled to an upper body of said subject;
   a lower limb orthotic component comprising at least one leg support configurable to be coupled to a first lower limb of said subject, with the at least one leg support including at least a thigh link rotatably connected to said torso portion at a hip joint, and a shank link rotatably connected to the thigh link at a knee joint;
   a first lower limb actuator for controlling motion of said hip joint; and
   a second lower limb actuator for controlling motion of said knee joint.

14. The method of claim 11, wherein said exoskeletal system comprises:
   a torso portion configurable to be coupled to an upper body of said subject;
   an upper limb orthotic component comprising at least one arm support configured to be coupled to a first upper limb of said subject, with the at least one arm support including at least an upper arm link rotatably connected to said torso portion at a shoulder joint, and a forearm link rotatably connected to the upper arm link at an elbow joint;
   a first upper limb actuator for controlling motion of said shoulder joint; and
   a second upper limb actuator for controlling motion of said elbow joint.

15. The method of claim 11, wherein said wearable powered orthotic system comprises:
   a torso portion configured to be coupled to an upper body of said subject; and
   a lower limb powered orthotic component configured to provide assistance in locomotion of a lower limb.

16. The method of claim 15, wherein said wearable powered orthotic system comprises:
   a plurality of sensors for monitoring positions of said lower limb powered orthotic component; and
   a controller configured to control assistance provided by said lower limb powered orthotic component.

17. The method of claim 11, wherein said wearable powered orthotic system comprises:
   a torso portion configured to be coupled to an upper body of said subject; and
   an upper limb powered orthotic component configured to provide assistance in locomotion of an upper limb.

18. The method of claim 17, wherein said wearable powered orthotic system comprises:
   a plurality of sensors for monitoring positions of said upper limb powered orthotic component; and
   a controller configured to control assistance provided by said upper limb powered orthotic component.

19. The method of claim 1, wherein said exoskeletal system is configured to perform one or more of:
   gait functions for the subject based on a predetermined level of assistance,
   gait functions where the level of assistance is adaptively varied based on performance of the subject,
   arm movements for the subject based on a predetermined level of assistance, and;
   arm movements where the level of assistance is adaptively varied based on performance of the subject.

20. The method of claim 1, further comprising administering to said subject at least one of:
   a neuromodulatory drug,
   a monoaminergic agonist,
   a monoaminergic agonist comprising a first agent selected from the group consisting of: a serotonergic drug, a dopaminergic drug, a noradrenergic drug, a GABAergic drug, and a glycinergic drug,
   a second agent selected from the group consisting of: 8-hydroxy-2-(di-n-propylamino)tetralin (8-OH-DPAT), 4-(benzodioxan-5-yl)1-(indan-2-yl)piperazine (S15535), N-{2-[4-(2-methoxyphenyl)-1-piperazinyl]ethyl}-N-(2-pyridinyl)cyclo-hexanecarboxamide (WAY 100.635), Quipazine, Ketanserin, 4-amino-(6-chloro-2-pyridyl)-1 piperidine hydrochloride (SR 57227A), Ondanesetron, Buspirone, Methoxamine, Prazosin, Clonidine, Yohimbine, 6-chloro-1-phenyl-2,3,4,5-tetrahydro-1H-3-benzazepine-7,8-diol (SKF-81297), 7-chloro-3-methyl-1-phenyl-1,2,4,5-tetrahydro-3-benzazepin-8-ol (SCH-23390), Quinpirole, and Eticlopride,
   a neuromodulatory drug that activates an α2c adrenergic receptor subtype and/or that blocks an α2a adrenergic receptor subtype,
   a neuromodulatory drug that activates an α2c adrenergic receptor subtype is 2-[(4,5-Dihydro-1H-imidazol-2-yl)methyl]-2,3-dihydro-1-methyl-1H-isoindole (BRL-44408),
   a neuromodulatory drug that is (R)-3-nitrobiphenyline and/or a compound according to the formula:

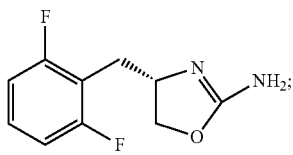 [SMILES: NC1=N[C@@H](Cc2c(F)cccc2F)CO1]

a neuromodulatory drug that is Clonidine, and
   a neuromodulatory drug that is a 5-HT1 and/or a 5-HT7 serotonergic agonist.

21. The method of claim 1, wherein said subject has at least one of:
   a motor complete spinal cord injury,
   a motor incomplete spinal cord injury,
   an ischemic brain injury,
   and
   a neurodegenerative pathology associated with one or more of: stroke, Parkinson's disease, Huntington's disease, Alzheimer's disease, amyotrophic lateral sclerosis (ALS), primary lateral sclerosis (PLS), dystonia, and cerebral palsy.

22. The method of claim 1, wherein said locomotor activity comprises standing and/or stepping.

23. The method of claim 1, wherein said locomotor activity comprises reaching.

* * * * *